(12) United States Patent
Zheng et al.

(10) Patent No.: US 9,370,736 B2
(45) Date of Patent: Jun. 21, 2016

(54) FLEXIBLE FILTER DEVICE FOR CAPTURING OF PARTICLES OR CELLS IN A FLUID

(71) Applicant: THE PENN STATE RESEARCH FOUNDATION, University Park, PA (US)

(72) Inventors: Siyang Zheng, State College, PA (US); Ramdane Harouaka, State College, PA (US); Mingda Zhou, State College, PA (US); Yin-Ting Yeh, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 605 days.

(21) Appl. No.: 13/744,051

(22) Filed: Jan. 17, 2013

(65) Prior Publication Data
US 2013/0180909 A1    Jul. 18, 2013

Related U.S. Application Data

(60) Provisional application No. 61/587,407, filed on Jan. 17, 2012.

(51) Int. Cl.
*B01D 29/52* (2006.01)
*B01D 33/37* (2006.01)
(Continued)

(52) U.S. Cl.
CPC .............. *B01D 29/52* (2013.01); *A61M 1/0056* (2013.01); *A61M 1/3633* (2013.01); *B01D 33/37* (2013.01); *B01D 63/087* (2013.01); *B01D 63/088* (2013.01); *B01D 2313/13* (2013.01)

(58) Field of Classification Search
CPC .... B01D 29/52; B01D 2221/10; B01D 33/00; B01D 33/041; B01D 33/29; B01D 33/35; B01D 33/37; B01D 63/08; B01D 2315/05; B01D 63/081; B01D 63/087; B01D 63/088; B01D 2313/13; A61M 1/0056; A61M 1/3633; A61M 1/0218; A61M 1/16; A61M 1/34; A61M 1/3482
USPC .................... 210/346, 645, 782, 486, 321.75, 210/321.84, 329, 354, 356, 500.22, 650, 210/651
See application file for complete search history.

(56) References Cited

U.S. PATENT DOCUMENTS

| | | | |
|---|---|---|---|
| 3,398,091 A | * | 8/1968 | Greatorex .............. B01D 53/22 159/1.1 |
| 3,464,562 A | * | 9/1969 | Martin ................... B01D 61/28 210/321.75 |

(Continued)

FOREIGN PATENT DOCUMENTS

| | | |
|---|---|---|
| CN | 101053683 | 10/2007 |
| CN | 102026698 | 4/2011 |
| CN | 101730572 | 3/2013 |

OTHER PUBLICATIONS

Lin et al., "Portable filter-based microdevice for detection and characterization of circulating tumor cells," Clin Cancer Res (2010) 16(20): 5011-5018.

(Continued)

*Primary Examiner* — Joseph Drodge
(74) *Attorney, Agent, or Firm* — Fox Rothschild LLP

(57) ABSTRACT

A filtering device includes a housing and one or more flexible filter arrays. The flexible filter arrays can be coupled to the housing. Each flexible filter array can include a plurality of members and one or more support members. The plurality of members each can have a proximal and a distal end, the plurality of members being spaced apart by a predetermined distance. The one or more support members can be coupled to one or more of the plurality of members. Each of the plurality of members can be configured to deflect relative to the one or more support members.

19 Claims, 16 Drawing Sheets

(51) Int. Cl.
*B01D 63/08* (2006.01)
*A61M 1/00* (2006.01)
*A61M 1/36* (2006.01)

(56) References Cited

U.S. PATENT DOCUMENTS

| | | | | |
|---|---|---|---|---|
| 3,520,803 | A * | 7/1970 | Iaconelli | A23F 5/285 159/DIG. 27 |
| 5,599,688 | A * | 2/1997 | Grass | B01D 61/18 324/450 |
| 5,601,727 | A * | 2/1997 | Bormann et al. | 210/767 |
| 7,846,393 | B2 | 12/2010 | Tai et al. | |
| 7,846,743 | B2 | 12/2010 | Tai et al. | |
| 7,955,504 | B1 * | 6/2011 | Jovanovic | B01D 61/18 210/321.71 |
| 8,114,289 | B2 | 2/2012 | Zheng et al. | |
| 8,288,170 | B2 | 10/2012 | Tai et al. | |
| 2001/0000204 | A1 | 4/2001 | Castino et al. | |
| 2003/0173285 | A1 * | 9/2003 | Schmidt | B01D 63/084 210/321.75 |
| 2005/0023207 | A1 * | 2/2005 | Kirker | B01D 63/00 210/321.74 |
| 2006/0254972 | A1 * | 11/2006 | Tai et al. | 210/321.6 |
| 2007/0025883 | A1 | 2/2007 | Tai et al. | |
| 2008/0206757 | A1 | 8/2008 | Lin et al. | |
| 2009/0188864 | A1 | 7/2009 | Zheng et al. | |
| 2010/0288690 | A1 * | 11/2010 | Rautio | B01D 63/08 210/347 |
| 2011/0053152 | A1 | 3/2011 | Goldkorn et al. | |
| 2011/0215045 | A1 | 9/2011 | Zhou et al. | |
| 2011/0244443 | A1 | 10/2011 | Van Rijn et al. | |
| 2012/0006760 | A1 | 1/2012 | Toner et al. | |

OTHER PUBLICATIONS

Lu et al., "Parylene membrane slot filter for the capture, analysis and culture of viable circulating tumor cells," Micro Electro Mechanical Systems (MEMS) IEEE 23rd International Conference (Jan. 24-28, 2010) p. 935-938.

Panchapakesan et al., "Micro- and nanotechnology approaches for capturing circulating tumor cells," Cancer Nano (2010) 1:3-11.

Ross and Slodkowska, "Circulating and disseminated tumor cells in the management of breast cancer," Am J Clin Pathology (2009) 132:237-245.

Xu, et al., "A cancer detection platform which measures telomerase activity from live circulating tumor cells captured on a microfilter," Cancer Res (2010) 70: 6420-6426.

Zheng et al., "3D microfilter device for viable circulating tumor cell (CTC) enrichment from blood," Biomed Microdevices (2011) 13: 203-213.

International Search Report and the Written Opinion of the ISA mailed on Apr. 23, 2013 in PCT Application No. PCT/US2013/021933, international filing date Jan. 17, 2013. (11 pages).

* cited by examiner

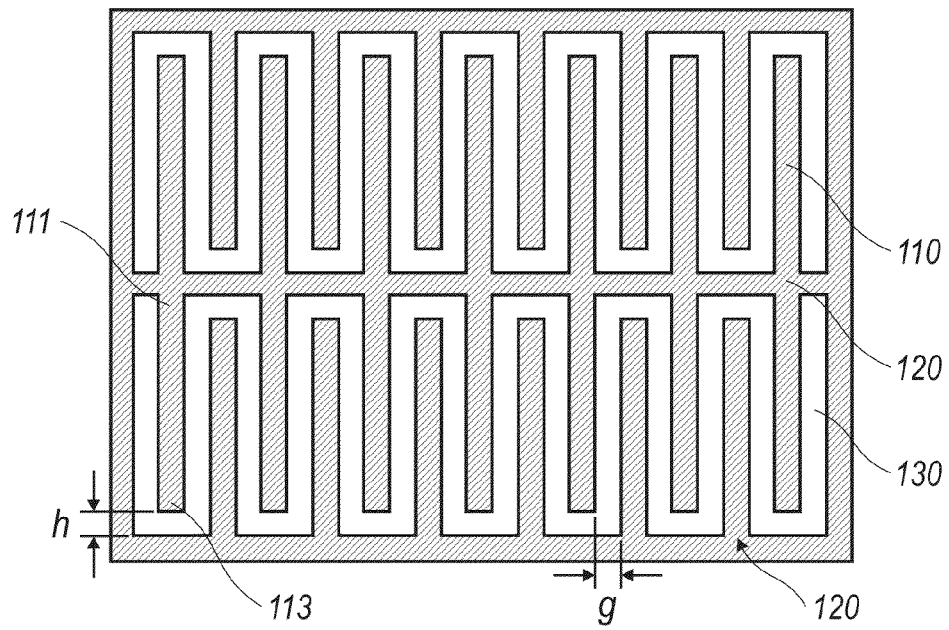
*FIG. 1C*
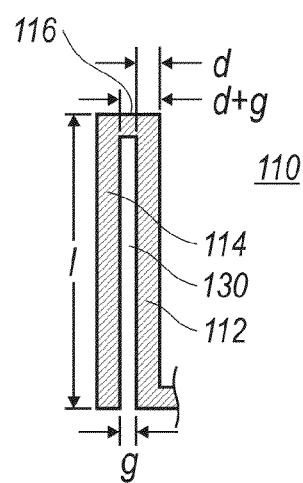
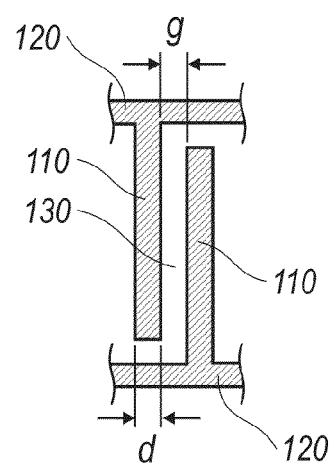
*FIG. 1B*          *FIG. 1D*

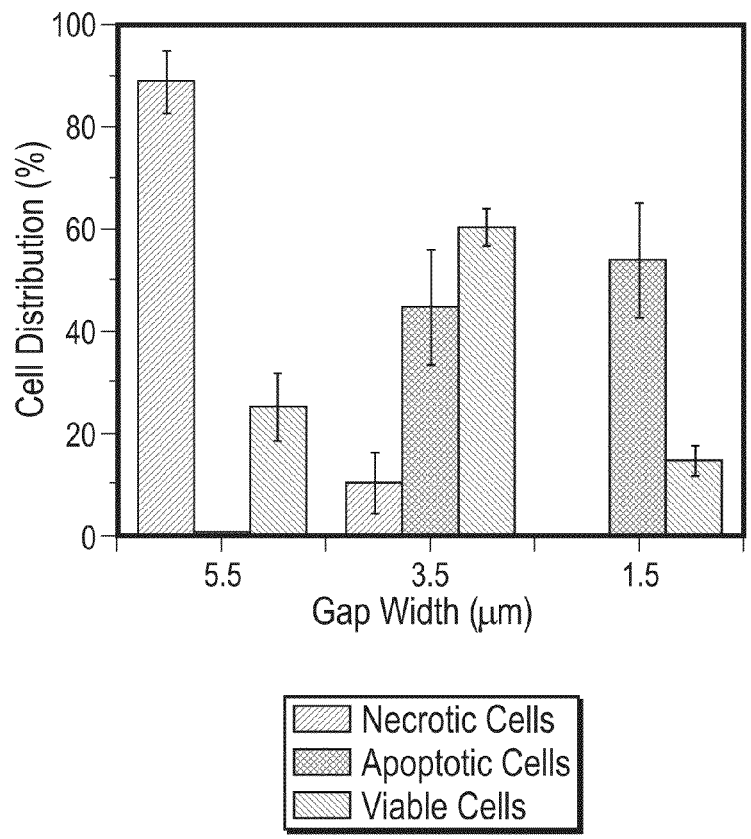
*FIG. 13C*
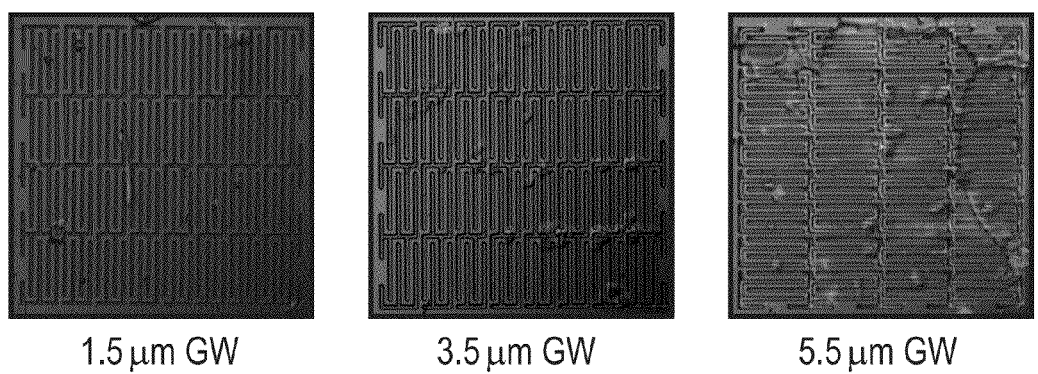
1.5 μm GW     3.5 μm GW     5.5 μm GW
*FIG. 13D*     *FIG. 13E*     *FIG. 13F*

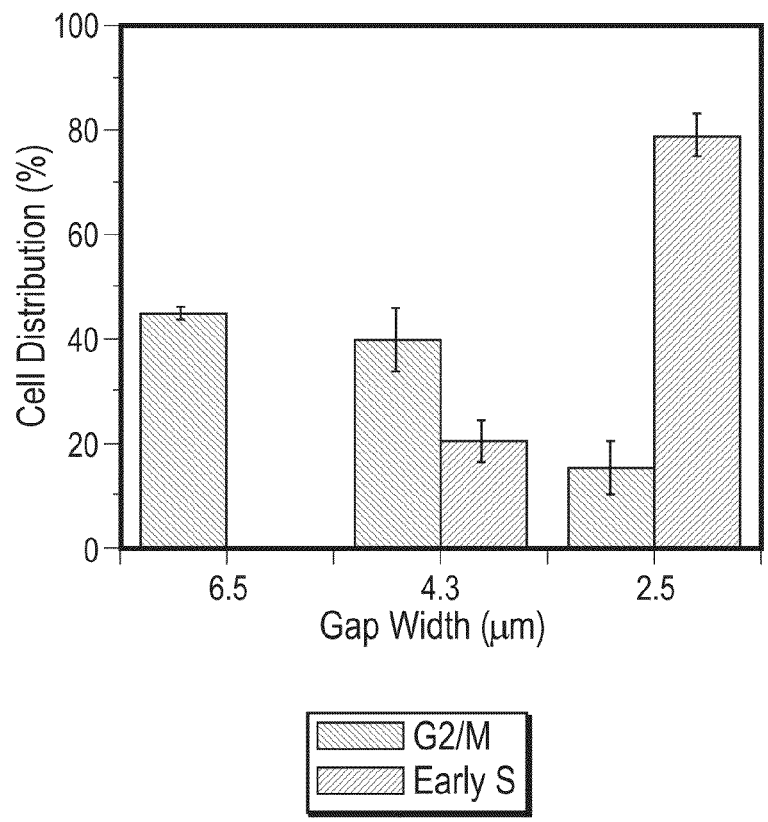
*FIG. 14C*
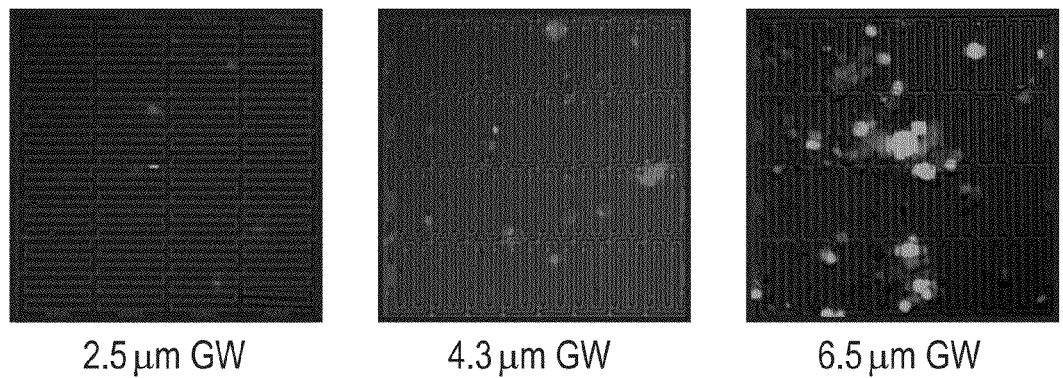
*FIG. 14D*   *FIG. 14E*   *FIG. 14F*

FLEXIBLE FILTER DEVICE FOR CAPTURING OF PARTICLES OR CELLS IN A FLUID

CROSS REFERENCE TO RELATED APPLICATION

This application claims priority from U.S. Provisional Pat. App. Ser. No. 61/587,407, filed on Jan. 17, 2012, the contents of which are incorporated herein in the entirety for all purposes.

FIELD

The subject matter herein generally relates to capturing particles in a fluid and specifically a bodily fluid.

BACKGROUND

Filtration is a process by which particles may be separated from a fluid or mixture of particles by taking advantage of differences in their physical properties. It occurs when a fluid is passed along or across a membrane or other structure that can act as a selective barrier. Particles are either retained by the barrier or pass through in the filtrate.

Since their invention in the 1960s track-etched polymer filters have been widely used for biological cell enrichment because of their low cost and fast sample processing speed. The track-etched filters have randomly distributed pores defined by swift heavy ions typically generated by nuclear reactors and then enlarged to a desired diameter in an etching process. These filters mechanically enrich certain cells from body fluids based on their ability to pass through pores of a particular size.

BRIEF DESCRIPTION OF THE DRAWINGS

Implementations of the present technology will now be described, by way of example only, with reference to the attached figures, wherein:

FIG. 1B is an illustration of a member of the flexible filter array illustrated in FIG. 1A;

FIG. 1C is an illustration of another implementation of a flexible filter array, including cantilevers, according to the present disclosure;

FIG. 1D is an illustration of a member of the flexible filter array illustrated in FIG. 1C;

FIGS. 13A-F illustrate an example of separation of viable, apoptotic and necrotic MDA-MB-231 cells by tandem flexible filter array device according to the present disclosure; and FIGS. 14A-F illustrate an example of separation of MDA-MB-231 cells synchronized at different stages of cell cycle according to the present disclosure.

DETAILED DESCRIPTION

Figure 1A:
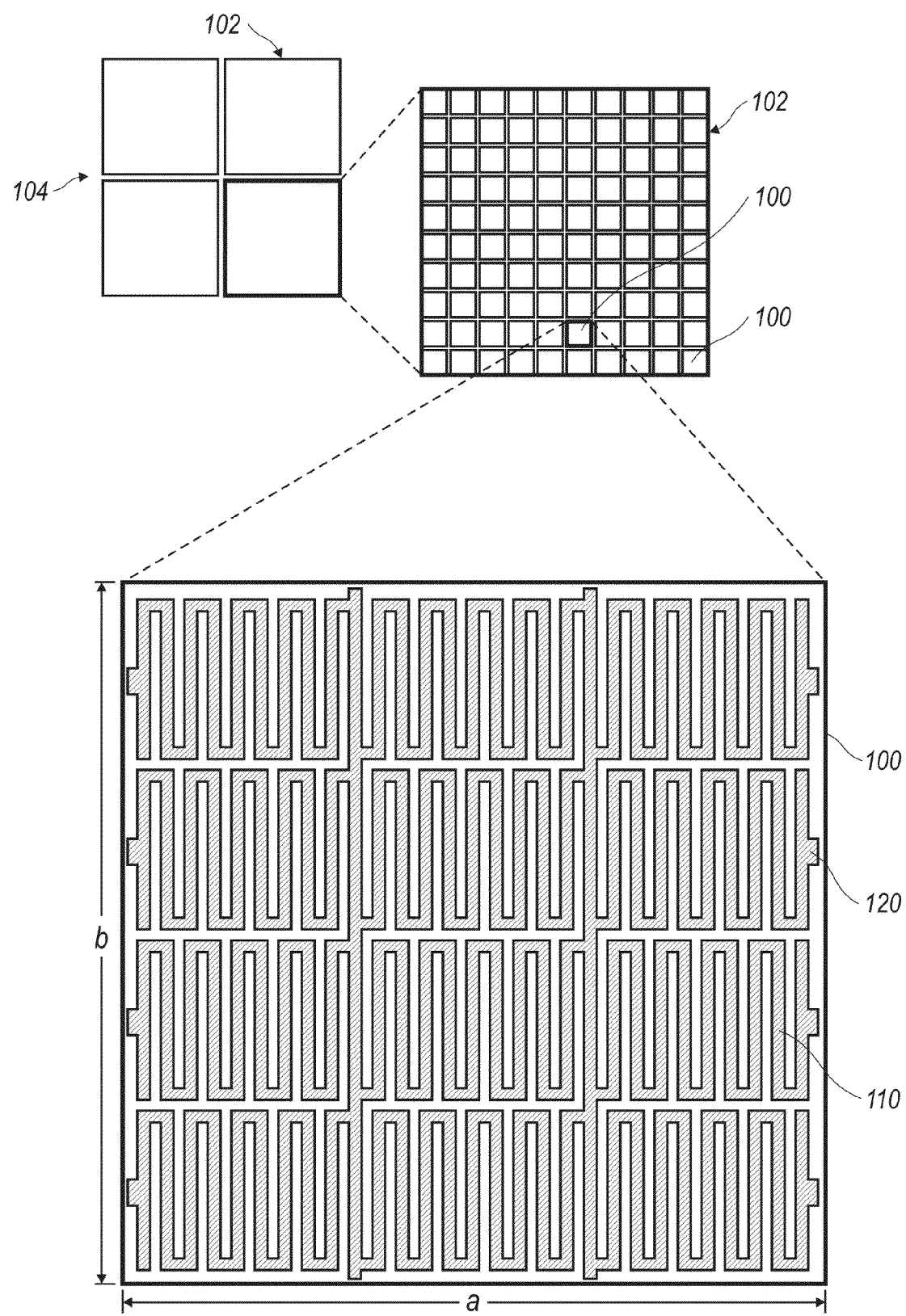
FIG. 1A is an illustration of an implementation of a flexible filter array, including micro-spring, according to the present disclosure.

For simplicity and clarity of illustration, where appropriate, reference numerals have been repeated among the different figures to indicate corresponding or analogous elements. In addition, numerous specific details are set forth in order to provide a thorough understanding of the implementations described herein. However, those of ordinary skill in the art will understand that the implementations described herein can be practiced without these specific details. In other instances, methods, procedures and components have not been described in detail so as not to obscure the related relevant feature being described. Also, the description is not to be considered as limiting the scope of the implementations described herein.

Several definitions that apply throughout this disclosure will now be presented.

The term "porosity" of a filter is defined here as the percentage of the open area on the two dimensional surface to the total surface area of the two dimensional surface.

The term "flexibility" generally refers to the stiffness of elastic materials characterized by their elastic modulus (Young's modulus). When referring to biological particles this definition takes into account their ability to deform in response to applied forces. When referring to device structural flexibility this definition also takes into account the ability of the structure to bend, flex and absorb stress due to applied forces.

The term cell "viability" refers to a cell's maintenance of its integrity, which can be determined by testing for membrane permeability to various chemicals using commercially available cell viability tests.

The term cell "proliferability" refers to the capability of a cell to replicate and form a colony. A viable cell might not be proliferable, as it can be in dormant state and not actively proliferating for the time of observation.

The term "capture efficiency/recovery" of a CTCs enrichment process is defined as the percentage of the number of tumor cells retained on device after enrichment to the number of tumor cells spiked in. To test capture efficiency/recovery of the CTC enrichment system, a model sample needs to be constructed by spiking a known number of tumor cells into healthy donor blood.

$$\text{Capture Efficiency} = \frac{\text{Number of tumor cells retained on device after enrichment}}{\text{Number of tumor cells spiked in}} \times 100\%.$$

The term "enrichment" of CTCs against leukocytes is defined as the ratio of tumor cells to leukocyte ratio after enrichment to that before enrichment.

$$\text{Enrichment} = \frac{(\text{Number of tumor cells}/\text{Number of leukocytes})_{after\ enrichment}}{(\text{Number of tumor cells}/\text{Number of leukocytes})_{before\ enrichment}}.$$

The term "coupled" is defined as connected, whether directly or indirectly through intervening components and is not necessarily limited to physical connections.

The present technology presents a filtering device. The filtering device as presented herein can include a housing and flexible filter array. The present technology contemplates the flexible filter array could be implemented with a variety of different arrangements that allow a fluid to flow across the flexible filter array. The flexible filter array can be coupled to the housing. The flexible filter array can include a plurality of members. In at least one implementation, each of the plurality of members can include a proximal and a distal end. The one or more members can be spaced apart by a predetermined distance. The distance of this spacing may be constant or it may be tapered in any dimension. The flexible filter array can include one or more support members. The one or more support members can be coupled to a support portion of the one or more of the one or more members. In at least one embodiment, the one or more members can be unsupported at a distal end. Additionally, the plurality of members can be configured to deflect relative to the support portion of the plurality of members. In another embodiment, both the proximal and distal ends of each of plurality of members can be configured to be coupled to a support member. In at least one embodiment, the distal end of the member can still deflect relative to the proximal end even when the distal end is coupled to a support member. Still further, the member itself can deflect relative to one or more of the support members.

A flexible filter array according to the present disclosure can operate on the principle of size based exclusion for the enrichment of circulating tumor cells (CTCs) from whole blood samples. Although, conventional track-etched microfilters and two dimensional (2D) pore shaped microfilters can be used for fixed blood samples, they are unsuccessful in enriching viable CTCs from blood as cells are damaged or lysed and lost in the flow-through. A flexible filter array 100 according to the present disclosure can use spring-like arrangements as the active structure for microfiltration. The spring-like geometry incorporates several important advantages over the pores in conventional microfiltration devices. The inherent flexibility of the spring structures allows for deformation in response to the application of flow pressure, thus reducing the initial impact between the cell and the device structure and relieving some of the tensile forces experienced by captured cells. The spring-like layout can also be designed to allow for maximal effective opening space, achieving an effective porosity of 20% or greater. The greater porosity increases the sample volume capacity and also eliminates problems with clogging that other microfilters experience. In this way the flexible filter array 100 can be used in conjunction with a precise pressure regulation system to limit the mechanical stresses experienced by cells during filtration.

FIG. 1A illustrates a flexible filter array 100 according to the present disclosure. The flexible filter array 100 can be incorporated into a first level array 102 comprising a plurality of flexible filter arrays 100. Furthermore, the first level array 102 can be incorporated into a second level array 104. As illustrated the first level array 102 includes one hundred flexible filter arrays 100. The flexible filter arrays 100 can include a plurality of members 110. As illustrated the flexible filter arrays 100 have a length (a) and a width (b). In the illustrated example, the length (a) and width (b) are the same, thereby forming a square. The depth (in/out of the paper) of the flexible filter array 100 can be uniform or it can vary. In the illustrated embodiment, the depth is uniform. In other embodiments, the depth can vary in a uniform or a non-uniform pattern so as to provide different flexibility characteristics. For example, it can be desirable to provide for a stiffer flexible filter array or a more flexible filter array which can be achieved by varying the thickness of the flexible filter array 100 while maintaining the other dimensions.

The second level array has four first level arrays that each measure 4.742 mm by 4.754 mm. Each first level array has a 10×10 array of flexible filter arrays 100. While the second level array is illustrated as having four first level arrays arranged as quadrants, the present technology can be implemented as a single first level array or with a pair of first level arrays. If a larger surface area is required, the second level array can include more than four first level arrays. In at least one embodiment, the number of additional first level arrays are combined in pairs when added. While the first level arrays as illustrated have the same shape and size, the shape and size of the first level arrays can vary.

The flexible filter array 100 can vary in size depending upon the desired stiffness and/or porosity. In the illustrated example, the length (a) of the flexible filter array can be between 0.5 cm and 1.5 cm. Likewise, the width (b) of the flexible filter array can be between 0.5 cm and 1.5 cm. The whole flexible filter array can be removed from the device housing and used as a culture site for those particles that are captured or located on the flexible filter array 100. Alternatively, patches of the flexible filter array can be selectively removed either by mechanical or thermal cutting or use micro laser dissection. In the latter case, a single cell or a single cluster of cells can be isolated before or after immunocytochemical detection with surface marker(s). In at least one embodiment, the flexible filter array 100 can be made of a material such as parylene-C or polydimethylsiloxane to allow the flexible filter array 100 to be implanted in a living organism. In other embodiments, the flexible filter array 100 can be made from a transparent, micromachinable thin film material. In still other embodiments, the flexible filter array 100 can be polylactic acid, polyglycolide, or any other micromachinable biodegradable material. The plurality of members can be in turn made from parylene-C, polydimethylsiloxane, a transparent, micromachinable thin film material, polylactic acid, polyglycolide, or any other micromachinable biodegradable material, or a combination thereof. The present disclosure contemplates the implementation of other materials that can be implanted as well. In other embodiments, where implantation is not required, the material of the flexible filter array can be selected based upon the desire to control the flexibility and other characteristics of the flexible filter array 100 as described herein. The material and device structural design can also be chosen to ensure that cells or other particles that impinge upon the flexible filter array 100 can survive the impact. In embodiments, where the fluid circulating through the flexible filter array 100 is returned to the organism from which it was obtained, the material can be selected for biocompatibility.

In one example, the flexible filter array 100 process can begin with the coating of a thin layer of transparent polymer on a silicon wafer through a deposition process. A metal can then be deposited onto the polymer film. The metal layer can be patterned using a photolithography technique and then etched with a suitable etching process. The patterned metal layer can be used as an etching mask for the underlying polymer layer. The desired pattern can be etched into the parylene layer by reactive ion etching using plasma. Finally the polymer layer can be released and cut into individual devices. In other embodiments, different construction methods and assemblies can be implemented in order to provide the filter having the flexible micro spring array according to the present teachings.

The plurality of members 110 as illustrated in FIG. 1A are in the form of flexible micro-springs. A flexible micro-spring as used herein refers to the arrangement of a member 110 in which the member 110 is arranged to act like a spring. In at least one example, the micro-spring can be arranged such that a one of the plurality of members 110 can be substantially parallel to another member 110. The members 110 can be joined by a connecting portion 116. The members 110 and connecting portion 116 can be substantially linear, as illustrated. In other embodiments, the members 110 and connecting portions 116 can be slanted or inclined. In yet other examples, the shape of the members 110 can be selected based upon the structure into which the flexible filter array 110 is to be installed for filtering. Additionally, the shape of the flexibility filter array 110 and members 110 can be chosen based upon whether the flexible filter array will be implanted or further removed for processing. In each row, the flexible micro-spring can be implemented with fourteen and a half turns of a spring-like shape.

An example of two members 110 is illustrated in FIG. 1B. As illustrated, the members 110 are arranged such that the left-hand member 114 can be substantially parallel to a right-hand member 112. The right-hand member 112 can be joined to the left hand member 114 by a connecting portion 116. The connecting portion 116 can join the right-hand member 112 and the left-hand member 114. The connecting portion 116 as illustrated can be substantially perpendicular to the right-hand member 112 and the left-hand member 114. As illustrated each member 110 has a width (d). In other embodiments, the width (d) of the member can vary for a given flexible filter array. For example, the width (d) can decrease from an outer edge of the flexible filter array 100 to an inner portion of the flexible filter array 100. The connecting portion 116 can also have a width (d). In at least one embodiment, the connecting portion 116 can have a length (g) which corresponds to the distance that the inner faces of the right-hand member 112 and left-hand member 114 are spaced apart. In at least one embodiment, the right-hand member 112 and left-hand member 114 can be between one-half (0.5) and two hundred (200) micrometers (μm). In another embodiment, the right-hand member 112 and left-hand member 114 can be between one (1) and fifty (50) micrometers (μm). In yet another embodiment, the right-hand member 112 and left-hand member 114 can be between three (3) and nine (9) micrometers (μm). The distance that the right-hand member 112 and left-hand member 114 are spaced apart can vary depending upon the size of the particle that is desired to be filtered from passing there through.

While the relationship between a right-hand member 112 and a left-hand member 114 has been described above, a similar relationship can apply to multiple members 110 that are adjacent to one another. As illustrated in FIG. 1A, the micro-spring can be formed in an adjacent pattern, such that two adjacent members 110 follow a similar pattern. In other embodiments, the shape and spacing can vary.

In the illustrated example of FIG. 1A, the flexible filter array 110 can include a plurality of members that are all joined together to form a single structure. In at least one embodiment, the single structure can be formed using a molding process. In another embodiment, the single structure can be formed by fastening or otherwise affixing the plurality of members 110 together via connecting members 116 and other components as described above.

The single structure includes a plurality of members 110 and other components. In the illustrated example of FIG. 1A, the single structure includes one hundred-sixteen (116) parallel members and one hundred-twelve (112) parallel connecting members. The parallel members 110 have a length that is greater than the connecting members 116. The connecting members 116 can be substantially orthogonal to the members 110. As illustrated, the parallel members 110 can be arranged in four rows that have a substantially uniform length. The rows can be joined together by row joining portions. In the illustrated example, the row joining portions of together with parallel members 110 can span across the flexible filter array 100. The four parallel members 110 and three row joining portions can span in a first direction across the flexible filter array 100 and form a spanning member. The spanning member can be coupled to a support structure via a two support members on each end of the spanning member. The spanning member can provide rigidity to the flexible filter array 100.

Another example of a flexible filter array 100 is presented in FIGS. 1C and 1D. As illustrated in 1C, the flexible filter array 110 includes a plurality of members 110. The plurality of members 110 can be substantially parallel to one another as illustrated. In another embodiment one or more of the plurality of members 110 can have a different orientation relative to one or more other ones of the plurality of members such that spacing between the different oriented member 110 and an adjacent member 110 can allow for a varying spacing between them.

The plurality of members 110 can be formed as cantilever members 110. The plurality of members can be formed such that the each member has a proximal end 111 and a distal end 113. When the plurality of members 110 can be arranged as cantilever members, the distal end 113 can be configured to flex relative to the proximal end 111. The proximal end 111 can be coupled to a support member 120. In at least one embodiment, such as the one illustrated, the support member 120 can form an outer perimeter of the flexible filter array 100. The support member 120 is shown as also spanning across the middle of the flexible filter array 100 in one direction. In another embodiment, another support 120 can be implemented to space across the middle of the flexible filter array 100 in another direction. In at least one embodiment, another direction can be substantially orthogonal to the one direction.

As illustrated the plurality of members 110 can be arranged in two rows. In other embodiments, the flexible filter array can have one row or more than two rows. Additionally, the length of the rows can vary such that the flexible filter array 100 can have a parallelogram shape or step-like shape. In at least one embodiment, the flexible filter array 100 can be arranged in a circular arrangement. As illustrated, adjacent members 110 can extend from a proximal end 111, wherein the proximal ends 111 of adjacent members can be located on support members that are opposed to one another such that the member 110 extend from one of the support members does not reach the other support member 120. The distance separating the distal end 113 from the opposing support member 120 is distance (h). In the illustrated example, the distance (h) separating the distal end 113 from the opposing support member can be substantially the same as the distance (g) separating adjacent members 110. In other embodiments, the distance (h) separating the distal end 113 from the opposing support member can be less than the distance (g) separating adjacent members 110. When the distance (h) is less than distance (g), the configuration can allow for a more uniform filtering of particles as it allows for the space under deflection of the member 110 to be the same. In another embodiment, the members 110 can have a tapered shape to allow for a more uniform gap space to be formed when the member 110 deflects. As illustrated, the members have a length (l).

FIG. 1D illustrates two adjacent members 110 of the flexible filter array 100 of FIG. 1C. As illustrated, the members 110 can be substantially parallel and straight with a width (d). In another implementation, the members 110 can be tapered from a proximal end 111 to the distal end 113, such that the distal end 113 has a width that is smaller than the width at the proximal end 111. When the adjacent members 110 are configured with a corresponding matching taper, the distance (g) between the adjacent members 110 can remain substantially the same along the length (l) of the members 110.

The following statements can apply to one or more of the above described embodiments/implementations. In at least one implementation, the plurality of members can be substantially rigid. In another implementation, the plurality of members can be substantially flexible. When the plurality of members are substantially rigid, the members can still flex or deflect. When the members are configured to flex or deflect, the members can absorb some of the impact from the particles colliding with the member. When the member is substantially flexible, the member 110 can be made shorter while retaining the desired flexibility for the flexible filter array. In at least one embodiment, the flexible filter array 100 can be configured to have a desired overall modulus of elasticity that is selected based upon the type of particles being captured.

The flexible filter array 100 can be configured to have a desired porosity. In at least one embodiment, porosity of the flexible filter array 100 is between twenty to sixty percent. In yet another embodiment, the porosity is between forty to sixty percent. In another embodiment, the porosity can be between fifty and sixty percent. Lower porosity is not ideal for this application because it reduces the sample capacity, for example maximal volume of blood that can be processed given the specific device surface area. Higher porosity can be eventually limited mainly by the fragility of the device structure.

The flexible filter array 100 can be implemented to filter a variety of fluids. In at least one implementation, the fluid can be a bodily fluid that contains cells, particles, other living organisms, and/or molecules. The creation of the filter array 100 can be designed based upon the cells, particles, other living organisms, and/or molecules that are desired to be filtered. For example, the cells, particles, other living organisms, and/or molecules can have a nominal smallest diameter or other dimension that is associated therewith. In some situations, where very small sizes of cells, particles, other living organisms, and/or molecules are desired to be filtered, two or more flexible filter arrays 100 can be arranged in series to reduce the chance of each of the flexible filter arrays 100 from becoming clogged.

The flexible filter array 100 as presented herein can be designed to operate at a low pressure. In one embodiment, the flexible filter array 100 can be designed to operate at a pressure less than 1245 Pa. In another embodiment, the flexible filter array 100 can be designed to operate at a pressure less than 800 Pa. In still another embodiment, the flexible filter array 100 can be designed to operate at a pressure less than 500 Pa. In yet another embodiment, the flexible filter array 100 can be designed to operate at a pressure less than 249 Pa. When the flexible filter array 100 is designed and configured to operate at these low pressures, the ability to capture and allow the molecules or particles to survive is greatly increased compared to other filters which require higher pressures to operate. Further still, when the flexible filter array 100 is configured to operate at one of the above pressures, it can achieve a flow rate between 0.1 mL/min and 50 mL/min.

Figures 2A, 2B:
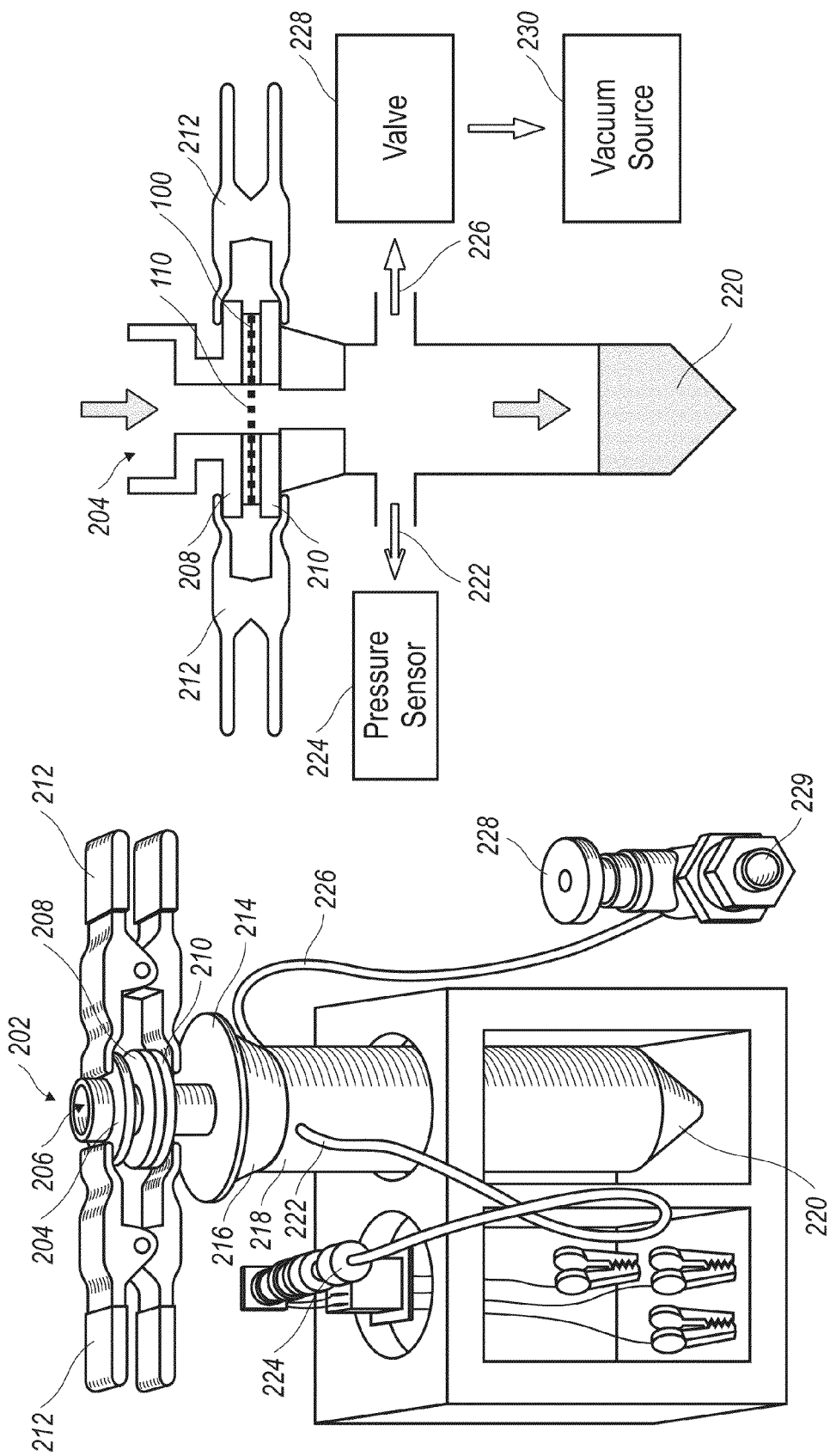
FIG. 2A is an illustration of an example of a filter arrangement according to present disclosure.
FIG. 2B is diagrammatic illustration of an example of a filter arrangement according to the present disclosure.

As indicated above, the flexible filter array 100 can be configured to capture or filter a variety of different size molecules and particles. FIGS. 2A and 2B illustrate a filter device 202 configured to receive the flexible filter array 100 as described above. In the illustrated example, the filter device 202 is configured to filter whole blood. The filter device 200 can be configured to filter other fluids including bodily fluids. An inlet 204 allows for the fluid to be received into the filter device. The fluid then passes through the flexible filter array 110. The fluid, particles, and molecules that are too small to be captured by the flexible filter array are collected in a collection area 220 of the filter device. In order to provide for a fluid flow, the filter device can include a suction outlet 226 which is coupled to a valve 228, which in turn can be coupled to a vacuum source. The vacuum source 230 can be configured to provide the desired pressure for the filter device 202. The filter device 202 can also include a pressure sensor outlet 222, the pressure sensor outlet 222 can be coupled to a pressure sensor 224. While the pressure sensor outlet 222 and suction outlet 226 can be in the form of tubes coupled to filter device 202, the pressure sensor outlet 222 and suction outlet 226 can take other forms such as threaded connections and other fluid coupling devices. In at least one embodiment, the pressure sensor 224 can be used to provide information that can be used to adjust the pressure in the filter device 202 by adjusting the valve 228 and/or the vacuum source. For example, the vacuum source can be configured to provide a fixed vacuum. By adjusting the position of the valve 228, the pressure in the filter device 202 can be varied. In one embodiment, the pressure sensor 224 can be coupled to the valve 228 via a controller so that the valve 228 can be adjusted automatically to maintain a desired pressure. Additionally, the controller can be configured to allow for a varying of the pressure if desired. When the filter device 202 includes a controller, the precision and accuracy in which the pressure is maintained inside of the filter device 202 can be increased. When the precision and accuracy of the pressure can be controlled enhanced ability to reduce the forces that the molecules and particles that are captured by the filter array 100 experience.

Figure 11:
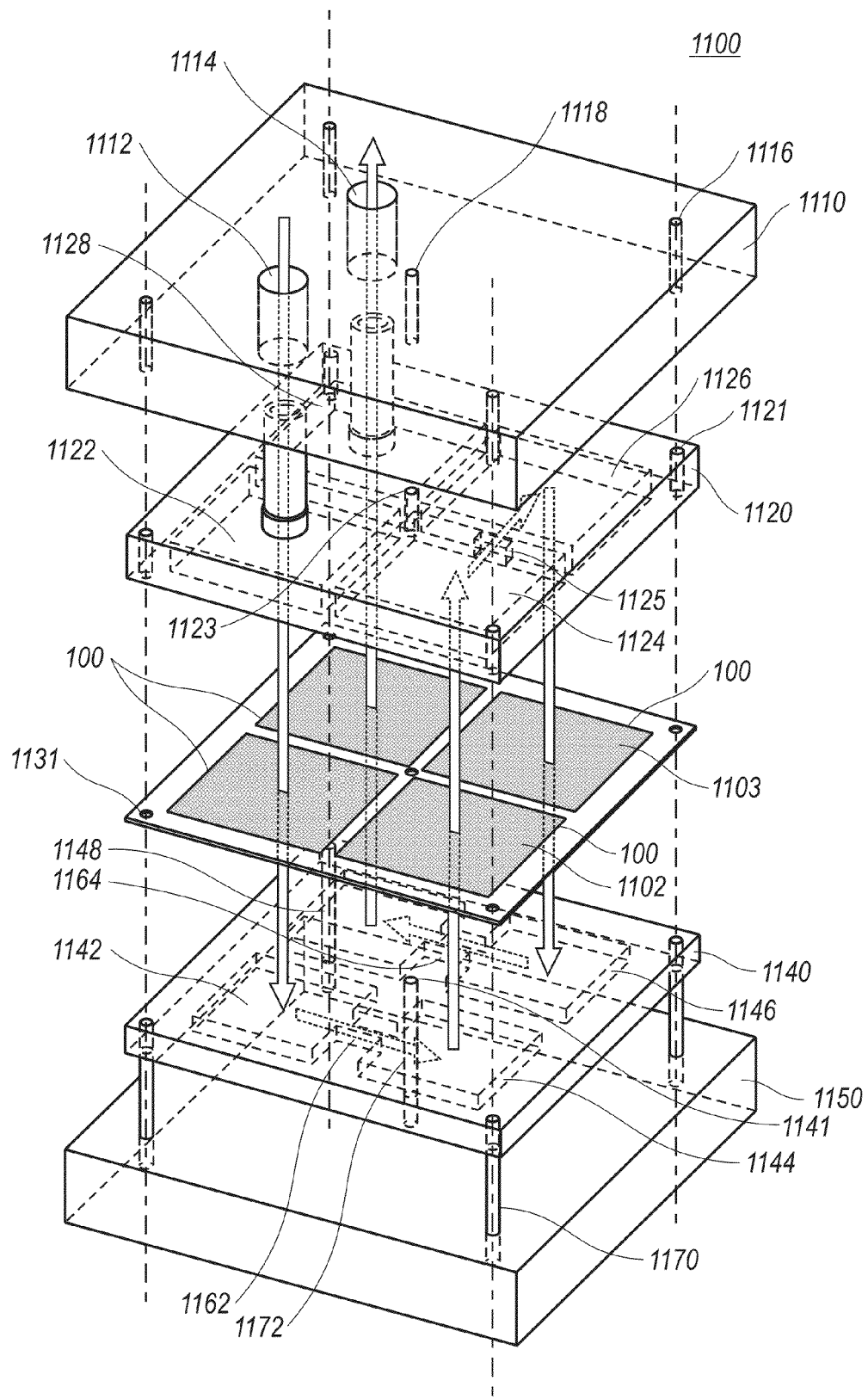
FIG. 11 illustrates an example of filtration assembly including four flexible filter arrays according to the present disclosure according to the present disclosure.
Figure 12A:
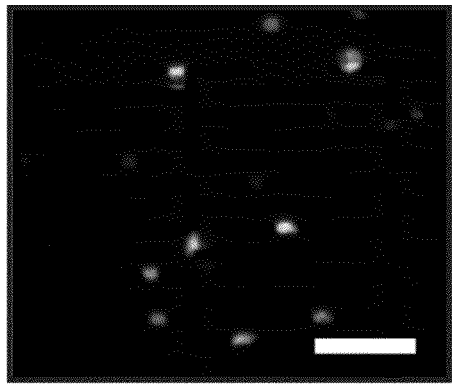
FIGS. 12A-D illustrate an example of tandem flexible filter array device for blood cell fractionation and separation according to the present disclosure.
Figure 12B:
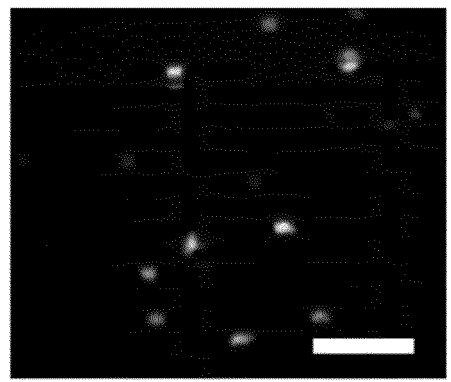
Figure 12C:
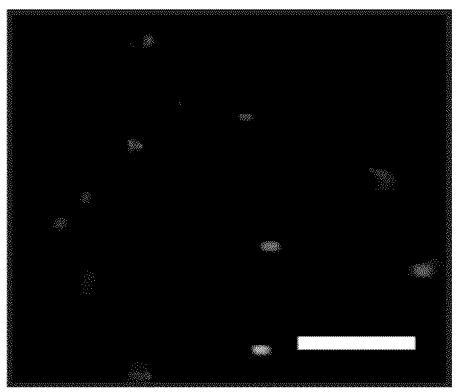
Figure 12D:
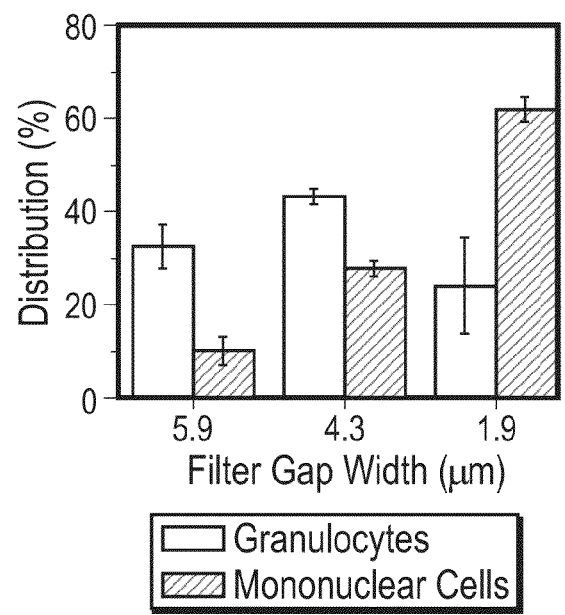

The flexible filter array 100 can be held in place through a variety of different configurations. As illustrated in FIG. 2A, the flexible filter (not shown) can be held between an upper plate 208 and a lower plate 210. The upper plate 208 and lower plate 210 can be held together by two clamps 212. The clamps 212 as illustrated can be configured to contact the bottom surface of the lower plate 210 and a top surface of a clamp plate 206. In the illustrated embodiment of FIG. 2B, the clamp plate 206 is eliminated and the clamps 212 contact the top surface of the upper plate 208 and the bottom surface of the lower plate 210. While the upper plate 208 and lower plate 210 are illustrated as having a circular perimeter, the upper plate 208 and lower plate 210 can have a perimeter that is of a variety of different shapes. The perimeter of the upper plate 208 and lower plate 210 can be configured to match the shape of the filter device 202 and/or provide for the desired fastening device. For example, the fastening devices as illustrated can include two clamps 212. In other embodiments, other fastening devices can be implemented. For example, bolts and screws can be implemented to couple the upper plate 208 to the lower plate. Another example of a filter device is illustrated in FIG. 11, as will be described below.

FIGS. 3A-10B illustrate various implementations of flexible filter arrays 100 according to the present disclosure. In the illustrated example, the flexible filter arrays 100 can be micro-spring filter arrays. These results are provided to provide an enhanced understanding to one of ordinary skill in the art the characteristics of flexible filter array 100 according to the present disclosure. In one example, a 1 cm² micro-spring filter array, according to the present disclosure, can process 7.5 mL of whole blood in under ten minutes at less than 1 inch water column (inch WC) driving pressure for each of the more than one hundred blood samples without clogging.

Figure 3A:
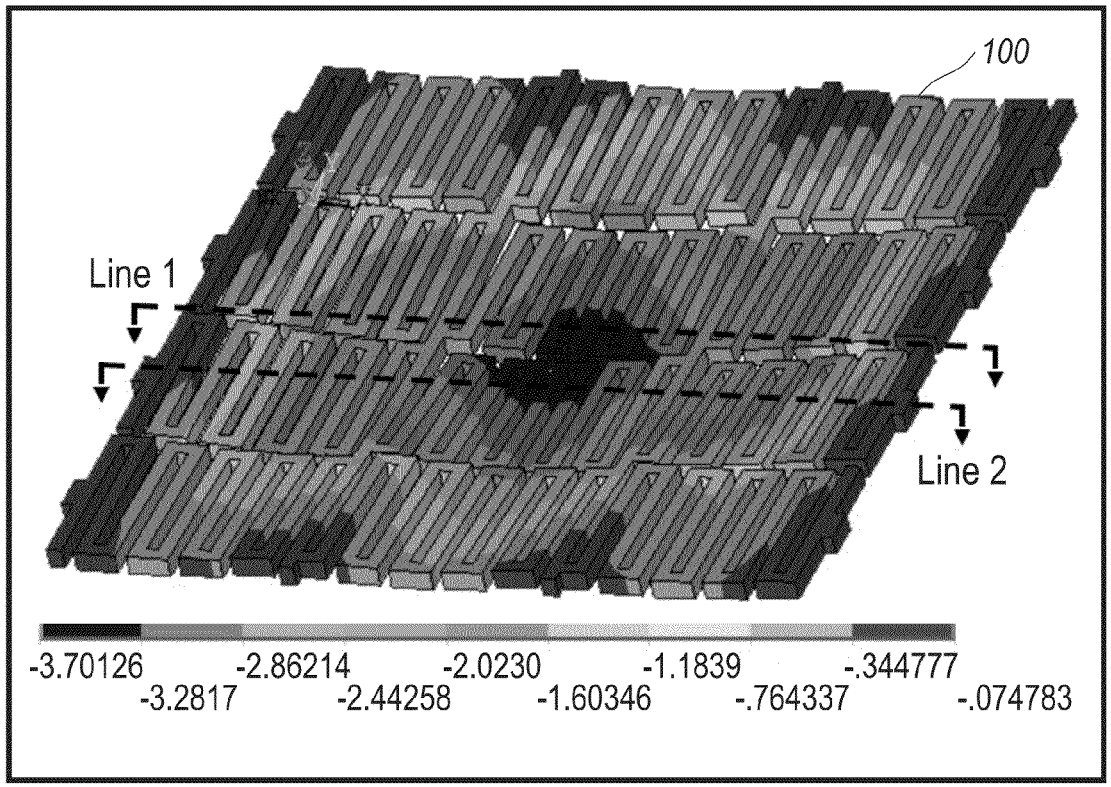
FIG. 3A is an illustration of a finite element simulation of the flexibility of a micro-spring flexible filter array illustrating out-of-plane displacement according to the present disclosure.

FIG. 3A illustrates a color coded out-of-plane displacement of an exemplarily micro-spring filter array under 0.1 psi pressure. Line 1 and Line 2 label positions for FIGS. 3F-G. FIGS. 3B-E illustrates geometric effects (member thickness t, member width d, member length and number of support member per array) on the maximal out-of-plane deformation of the exemplarily micro-spring filter array of FIG. 3A, wherein the circle denotes the geometric parameters used in a specific implementation of the micro-spring filter array. FIGS. 3F-G illustrate exemplarily gap width changes measured from top and bottom of the gaps along Line 1 and Line 2 of the micro-spring filter array of FIG. 3A.

In the example, the micro-spring filter array was designed as a single layer parylene membrane with flexible spring-like structures capable of deformation in response to applied stress. The stiffness of the micro-spring filter array can be controlled by the member length l, the member thickness t, the member width d and the number of anchor pairs n. A model of the system was created to perform finite element analysis. Finite element analysis was carried out to study the effects of these geometric parameters on the micro-spring filter array flexibility. Boundary conditions were applied to the surface of the anchors that connect the members to the frame and all six degrees of freedom were restricted. The Young's modulus and Poisson's ratio of the member material was set to be 2.76 GPa and 0.4, respectively. A uniform pressure of 0.1 pounds per square inch (psi) equivalently 2.77 inch WC was applied to the top surface of the micro-spring filter array. The maximal out-of-plane deformation was calculated in post-processing. Each of the four geometric parameters was studied independently while keeping the other three at the final design values. The design values, as illustrated in FIG. 3A, for these four studied geometric parameters are: member thickness t=10 μm, member width d=8 μm, member length l=80 μm, and number of anchors=2. These values are illustrated as the data points that are circled in FIGS. 3B-3E.

Figure 3B:
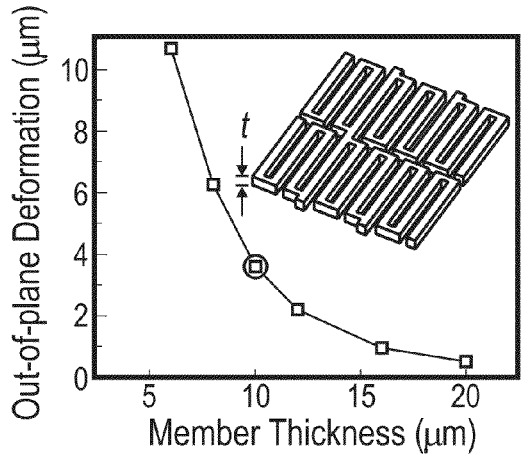
FIG. 3B is a graphical illustration of out-of-plane deformation of an example micro-spring vs. member thickness according to the present disclosure.

In FIG. 3B, the influence of the member thickness t on the out-of-plane deformation of the micro-spring array was examined. As the member thickness increases from 6 to 20 μm, the deformation decreases dramatically from 10.7 to 0.6 μm. Thus, the member thickness is a parameter that can be used to significantly change the flexibility of the micro-spring array during fabrication for a given mask design.

Figure 3C:
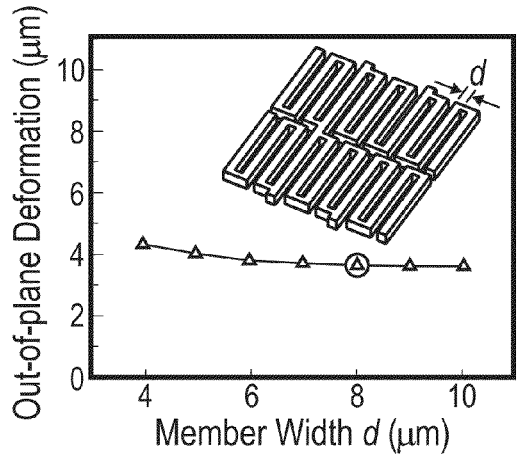
FIG. 3C is a graphical illustration of out-of-plane deformation of an example micro-spring vs. member width according to the present disclosure.

In FIG. 3C, the influence of member width d was examined, while keeping the periodicity d+g as a constant. The maximal out-of-plane deformation decreases slightly as the member width increases. The member width alone appears to have very small impact on the out-of-plane deformation.

Figure 3D:
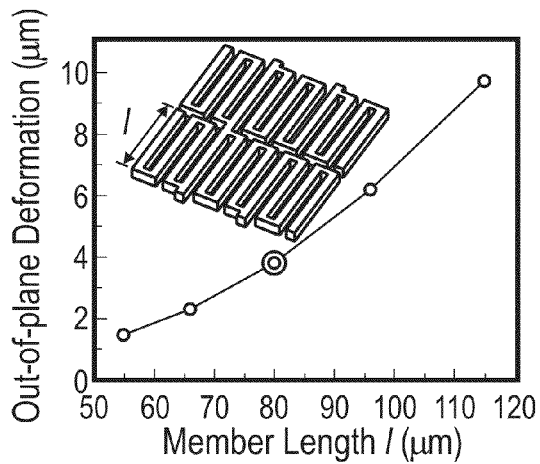
FIG. 3D is a graphical illustration of out-of-plane deformation of an example micro-spring vs. member length according to the present disclosure.

In FIG. 3D, the influence of member length 1 was examined. The simulation results of changing member length l shows the maximal out-of-plane deformation increases as the member length l increases.

Figure 3E:
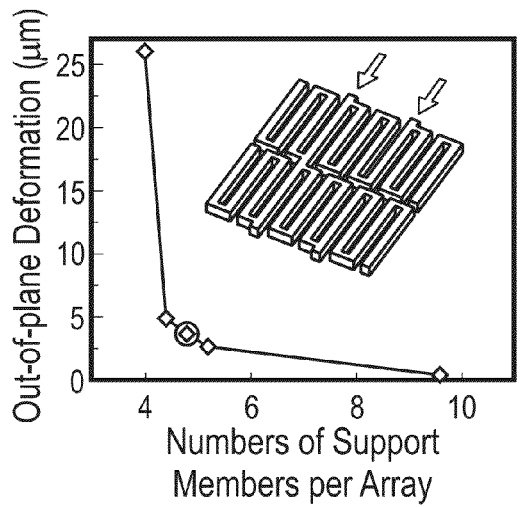
FIG. 3E is a graphical illustration of out-of-plane deformation of an example micro-spring vs. number of anchors per array according to the present disclosure.
Figure 3F:
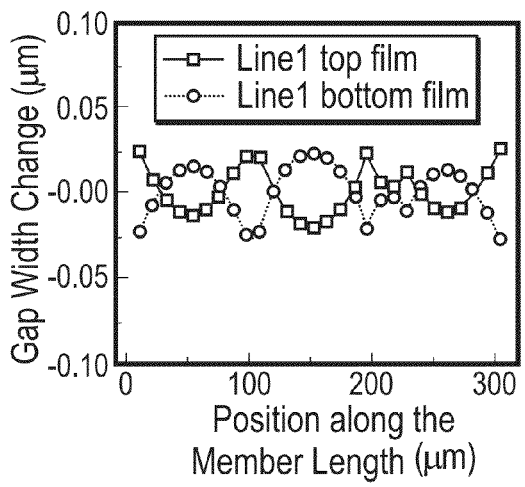
FIG. 3F is a graphical illustration of gap width change of an example micro-spring vs. position along the member length for line 1-1 of FIG. 3A.
Figure 3G:
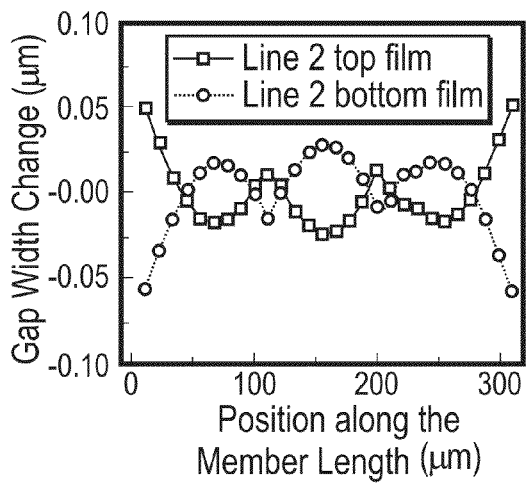
FIG. 3G is a graphical illustration of gap width change of an example micro-spring vs. position along the member length for line 2-2 of FIG. 3A.

FIG. 3E illustrates the influence of the number of anchors per array has on the out-of-plane deformation.

Using a load-deflection relationship for a rectangular membrane, the calculated effective Young's modulus of a single micro-spring array (or the structure rigidity) is 44 MPa, which is about two orders of magnitude smaller than that of material itself. Perforation of the material only reduces the effective Young's modulus proportional to the porosity, and this significant reduction of the effective Young's modulus is due to the flexible micro-spring array.

Contrary to the out-of-plane deformation, the in-plane deformation and the change of gap width due to the applied pressure were found to be inconsequential. For the final design parameters, the maximal gap width change under 0.1 psi was less than 60 nm. Since the gap width changes are so small, the micro-spring array is expected to effectively maintain a constant gap width during enrichment.

FIGS. 3F and 3G illustrate the in-plane filter structure deformation, i.e. the change of gap width, at different positions of the filter patched being simulated. The simulation illustrates that the change of the in-plane gap width is orders of magnitude smaller that the out-of-plane deflection of the flexible structure.

Figure 4A:
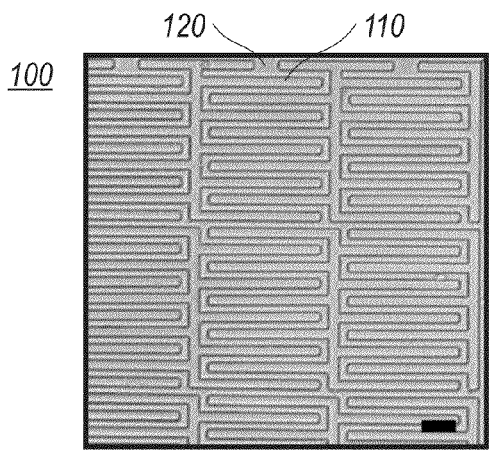
FIG. 4A is an example of a micro-spring flexible filter array according to the present disclosure.
Figure 4B:
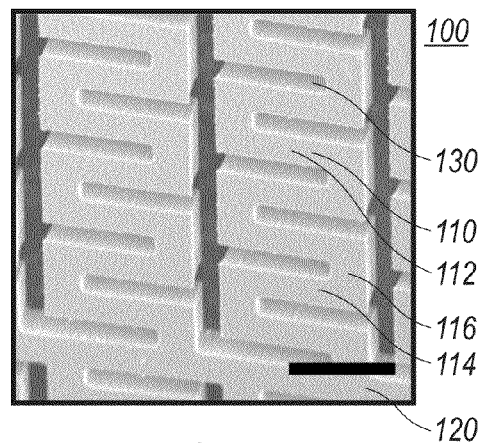
FIG. 4B is an example of a micro-spring flexible filter array according to the present disclosure.
Figure 4C:
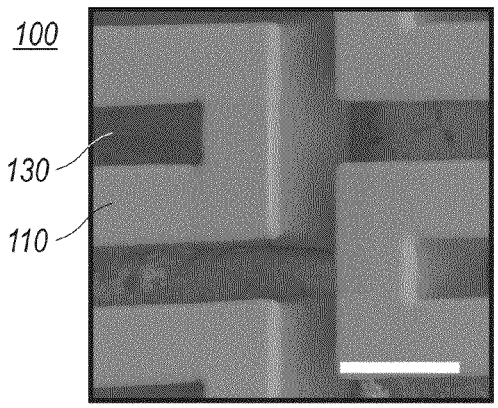
FIG. 4C is an example of a micro-spring flexible filter array according to the present disclosure.
Figure 4D:
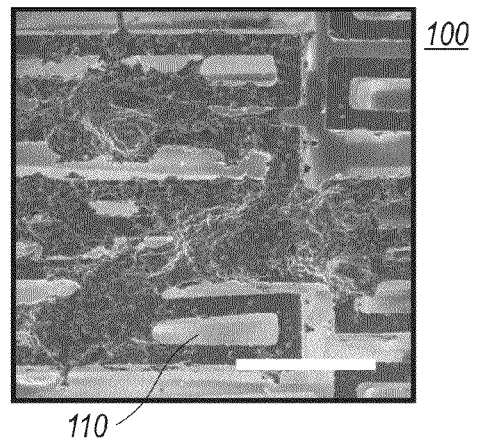
FIG. 4D is an example of a micro-spring flexible filter array, including one or more tumor cells, according to the present disclosure.

FIG. 4A illustrates a bright field optical microscopic image of an area of an exemplarily micro-spring filter array. FIG. 4B illustrates an SEM image of an exemplarily micro-spring filter array with shorter spring width than the micro-spring filter array illustrated in FIG. 4A. FIG. 4C illustrates a SEM image of an exemplarily micro-spring filter array after refill. FIG. 4D illustrates a SEM image showing tumor cell growth on an exemplarily micro-spring filter array. Scale bars for FIGS. 4A, 4B and 4D are 30 μm. Scale bar for FIG. 4C is 10 μm.

Figure 5A:
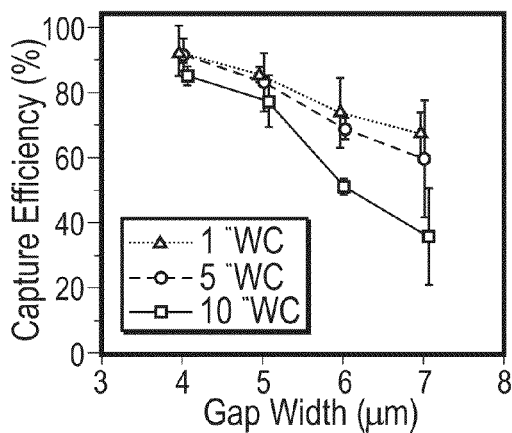
FIG. 5A illustrates a graph of capture efficiency vs. gap width for an example of a micro-spring flexible filter array at different pressures according to the present disclosure.
Figure 5B:
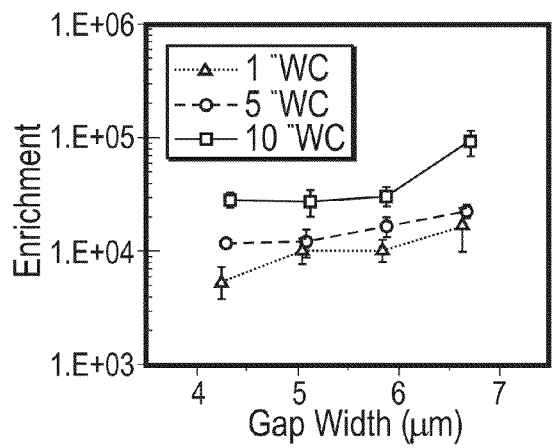
FIG. 5B illustrates a graph of enrichment vs. gap width for an example of a micro-spring flexible filter array at different pressures according to the present disclosure.

FIG. 5A illustrates capture efficiency under exemplarily gap widths and driving pressures. In the illustrated example, four carcinoma cell lines (MCF-7, MDA-MB231, C8161, WM35) were used separately using model systems. A known number of pre-labeled cells was spiked in healthy donor blood and processed to determine recovery rates. Each data point shows the mean value and its standard deviation (n≥3). FIG. 5B illustrates enrichment of whole blood under exemplarily gap widths and driving pressures. The number of leukocytes that remained after enrichment of whole blood was quantified through microscopy and image analysis then compared to the known initial leukocyte count to determine an enrichment ratio. Each data point shows the mean value and its standard deviation (n=3).

Figure 6:
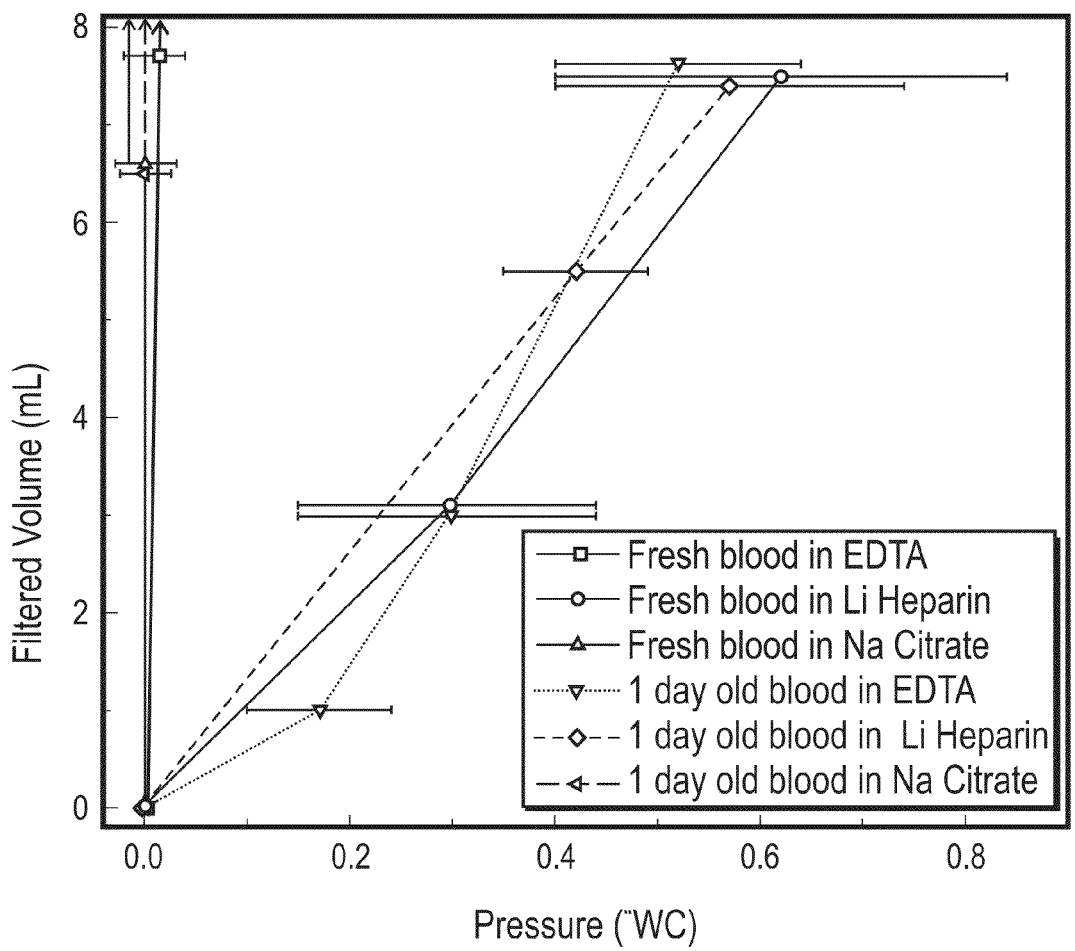
FIG. 6 illustrates a graph of filtered volume vs. pressure using various blood products according to the present disclosure.

FIG. 6 illustrates the effects of the freshness of blood samples and the types of anticoagulant on the blood volume that can be processed through an exemplarily 1 cm×1 cm micro-spring filter array. The filtered volumes were the blood volumes that were tested. For the cases of sodium citrate as the anticoagulant and fresh blood in EDTA (labeled with upward arrows), the driving pressures were so low and the tested blood volumes are expected to be lower than the maximal volumes that can be processed. The rest of the data points represent the maximal blood volumes that can be processed under the specified pressure for the specified anticoagulants and blood storage times.

Figure 7:
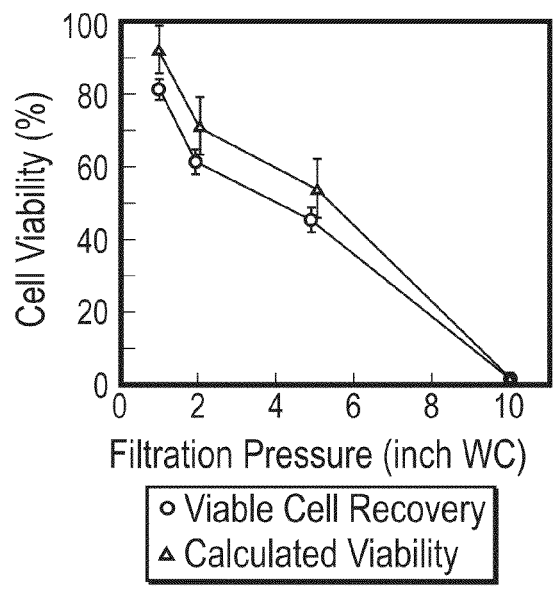
FIG. 7 is a graph of viability vs. pressure according to the present disclosure.
Figure 8A:
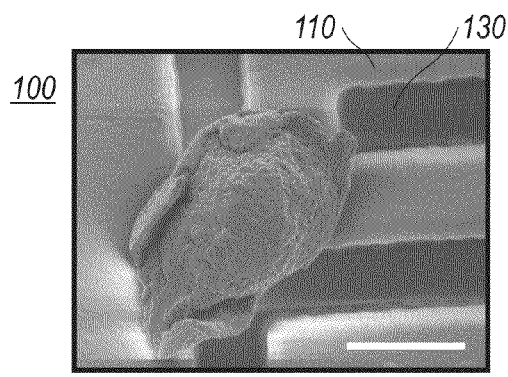
FIG. 8A illustrates a scanning electron microscope (SEM) image of an example enrichment under one inch of water column pressure according to the present disclosure.
Figure 8B:
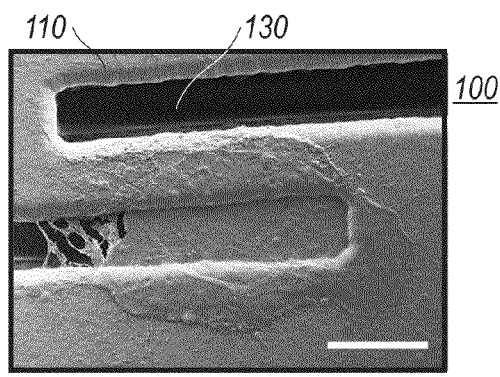
FIG. 8B illustrates a SEM image of an example enrichment under ten inches of water column pressure according to the present disclosure.

In FIG. 7, an exemplarily effect of pressure on cell viability is shown for a 5 μm gap micro-spring filter array. Calcein AM dye and Ethidium Homodimer-1 were used to assay MDA-MB 231 cell membrane integrity after enrichment from 1 mL of whole blood at various driving pressures. Viable cell recovery was determined as the percentage of viable cells retained out of the total number of cells spiked into the blood. Calculated viability is presented as the viable cell recovery divided by the known capture efficiency for MDA-MB 231 cells at each pressure condition. Limiting the driving pressure to 1 inch water column allowed a viable cell recovery of >80%, which corresponds to a calculated viability of >90%. 5 inch water column driving pressure lowered viable cell recovery to below 50% and 10 inch water column pressure effectively prohibited any viable cell capture FIG. 8A illustrates an exemplarily enrichment under 1 inch water column pressure. FIG. 8B illustrates exemplarily enrichment under 10 inch water column pressure. Scale bars in both FIGS. 8A and 8B are 10 μm.

Figure 9A:
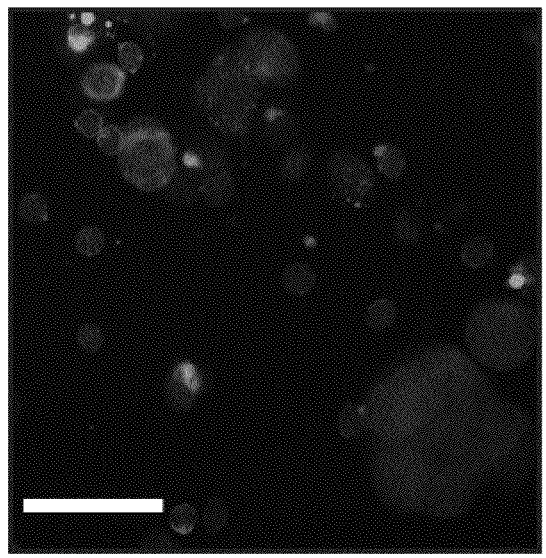
FIGS. 9A-D illustrate immunocytochemical detection of circulating tumor cells on micro-spring flexible filter arrays according to the present disclosure.
Figure 9B:
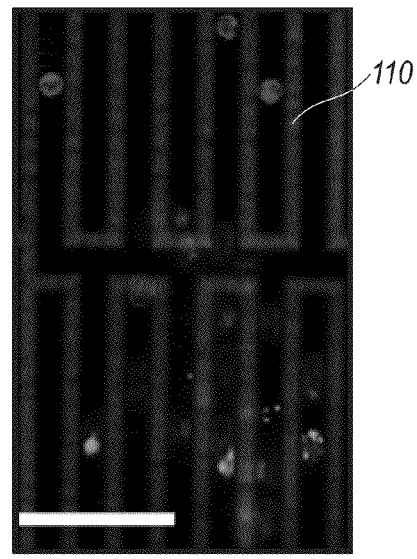
Figure 9C:
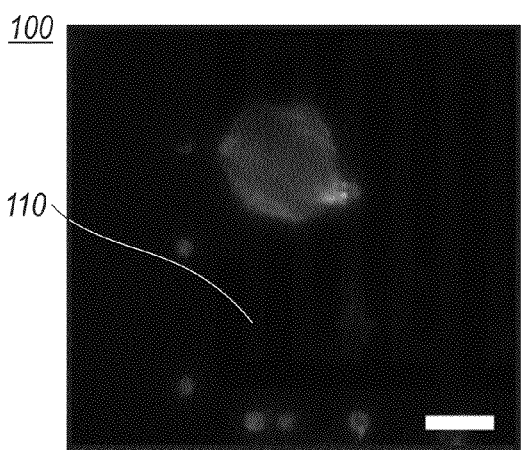
Figure 9D:
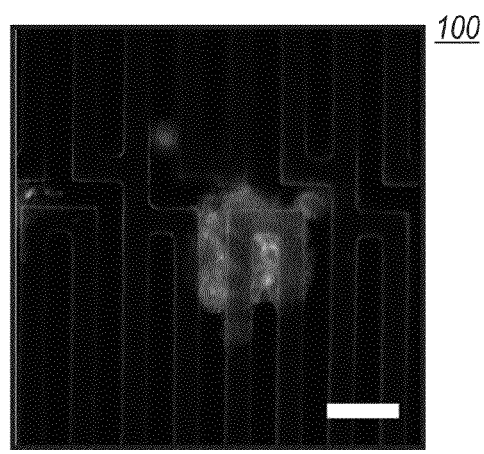

FIG. 9A illustrates an exemplarily positive control of a spiked sample on glass slides. FIG. 9B illustrates an example positive control of a spiked sample after exemplarily enrichment by the micro-spring filter array. FIG. 9C illustrates an example of a single CTC enriched from a clinical sample. FIG. 9D illustrates a cluster of CTCs enriched from another clinical sample. Scale bars are 20 μm.

Immunofluorescent detection was established to identify CTCs from clinical samples after enrichment with the micro-spring filter array. As positive controls, MDA-MB 231 cells were spiked into 1 mL of peripheral blood and either deposited on glass slides (FIG. 9A) or filtered through the device (FIG. 9B). The protocol described herein was used to stain the cells with monoclonal antibodies for cytokeratins and CD45. The MDA-MB 231 cells were observed as large nucleated cells that stained positively for cytokeratins and negatively for CD45. The contaminant leukocytes were noticeably smaller in size, and stained positively for CD45 and negatively for cytokeratins.

Successful immunofluorescent detection was then demonstrated with clinical samples. An example of a CTC detected from a patient diagnosed with Stage IV Non-Small Cell Lung Cancer is shown in FIG. 9C. 7.5 mL of blood was filtered through the device and stained using the previously described immunofluorescent detection process. FIG. 9D shows an aggregate cluster of 3 CTCs and 3 leukocytes obtained using the same process from a Stage IV Breast Cancer patient. Aggregate clusters of CTCs have been previously reported in Lung Cancer patients and Breast Cancer patients.

Figure 10A:
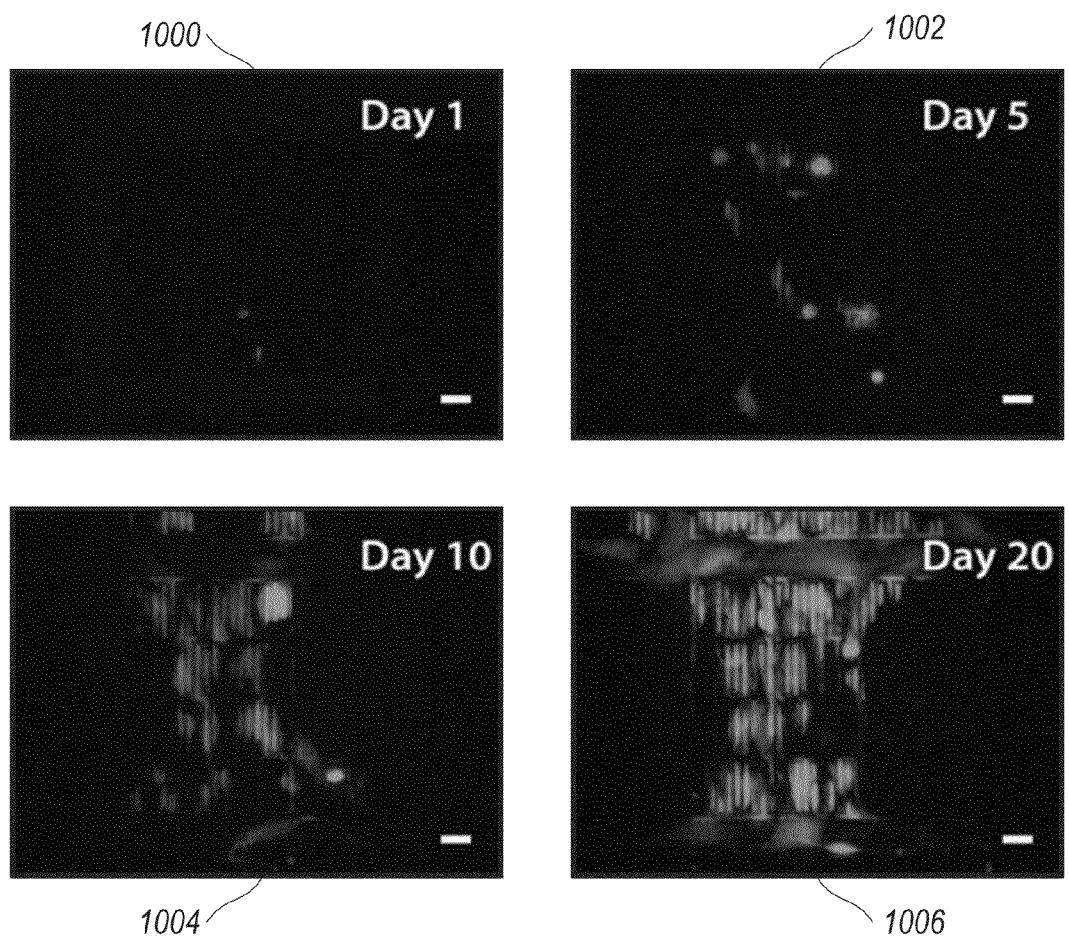
FIG. 10A illustrates an example of colony expansion of GFP labeled C8161 melanoma cells on the micro-spring flexible filter array, according to the present disclosure.
Figure 10B:
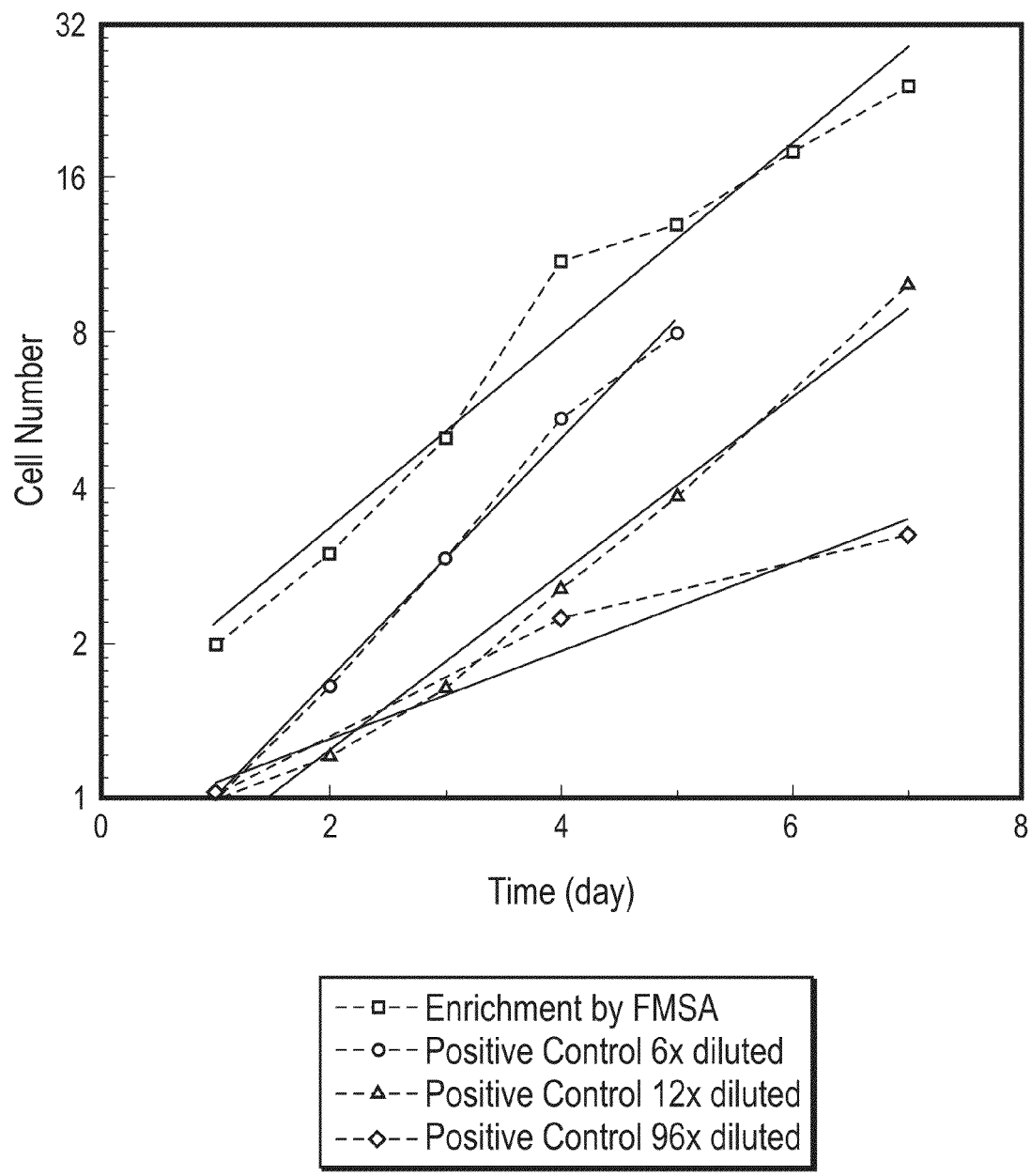
FIG. 10B illustrates an example of cell number over time for cell proliferation on the micro-spring flexible filter array and in Petri dishes (as positive controls) according to the present disclosure.

FIG. 10A illustrates an example of colony expansion of GFP labeled C8161 melanoma cells on the micro-spring array. Cells are spiked in blood, enriched with the micro-spring filter array and cultured on-chip. Pictures are fluorescent images of the same micro-spring filter array area over time. Scale bars are 50 μm. FIG. 10B illustrates an example of cell number over time for cell proliferation on the micro-spring filter array and in Petri dishes (as positive controls). Positive controls of cell proliferation are at various initial seeding levels (6×, 12×, and 96× dilutions). Log phase growth curves are linearly fitted in a semi-log plot as solid lines to extract the population doubling time.

FIG. 11 illustrates another example of the filter device 1100 that incorporates a plurality of the flexible filter arrays 100 in series to form the tandem flexible filtration device. As illustrated, the filter device 1100 includes four different flexible filter arrays 100 arranged in series. In one embodiment, the size of the gap widths g of each of the flexible filter array 100 is different from the other flexible filter array 100 of the filter device 1100. When different gap spaces g are arranged in series as shown, it is possible to capture different materials, cells, blood cells, subtype of blood cells, stem cells circulating tumor cells, microbes, metabolic aggregates on each of the flexible filter arrays 100. For example, the flexible filter array 1101 with the largest gap space g is placed first in the series of the flexible filter arrays 100 allowing the first flexible filter array 1101 to capture the largest materials, particles, cells, and circulating tumor cells. The next flexible filter array 1102 can be sized smaller than the first flexible filter array 1101 to capture the materials, particles, cells, and circulating tumor cells. Likewise, each successive flexible filter array 100 can be sized such that the respective gap space g is smaller than the previous flexible filter array 100. In at least one embodiment, two or more of the flexible filter arrays 100 can have the same gap space. For instance the last two flexible filter arrays (1103, 1104) can have the same gap size g. This can be done to increase the capture rate of the most desired materials, particles, cells, and circulating tumor cells. Alternatively, the first two flexible filter arrays (1101, 1102) can have the same gap size g so as to prevent the larger materials, particles, cells, and circulating tumor cells from clogging the next size flexible filter array 100.

The filter device 1100 as shown is constructed using a top layer 1110 that provides for ingress and egress of the fluid to be filtered. For example, the fluid can be blood or water. Other fluids are considered within the scope of this disclosure. The top layer has two ports (1112, 1114) that can be configured to accommodate various connectors. One of the ports is an inlet port 1112, and the other port is an outlet port 1114. The top layer 1110 can also include one or more perimeter attachment devices 1116. The perimeter attachment devices 1116 are pin receivers that receive a pin 1170. Additionally, the top layer can include a center attachment device 1118. As illustrated the center attachment device is in the form of a pin receiver that is configured to receive a center pin 1172. In at least one embodiment, the top layer 1110 can be a plastic layer. In other embodiments, the top layer 1110 can be a glass or metal layer.

The next layer is a top chamber layer 1120. In at least one embodiment, the top chamber layer can be made of Polydimethylsiloxane (PDMS). In other embodiments, the top chamber layer can be made of rubber, plastic or other type of polymer. The top chamber layer 1120 accommodates the fluid upon entrance or exit from the respective flexible filter array 100. As illustrated there are four top chambers formed in the top chamber layer 1120. A first top chamber 1122 receives the fluid from the inlet port 1112. A second top chamber 1124 receives fluid after it has passed through the first flexible filter array 1101 and a second flexible filter array 1102. The third top chamber 1126 receives fluid from the second top chamber 1124 via a upper coupling port 1125 that is formed in the second layer 1120 between the second top chamber 1124 and the third top chamber 1126. The fourth top chamber 1128 receives the fluid after it has passed through all four flexible filter arrays 100 and prior to exiting the filter device 100 through the exit port 1114. The top chamber layer also has perimeter coupling devices 1121 and a center coupling device 1123. The perimeter coupling devices 1121 and the center coupling device 1123 are the in form of through holes that are configured to receive pins 1170 and a center pin 1172, respectively. Other coupling devices can be implemented as well.

The third layer 1130 can be a flexible filter layer. The third layer in at least one embodiment can be constructed as a single sheet. In another embodiment, the flexible filter arrays 100 are formed separately and then bonded to the third layer 1130. The third layer 1130 can also include perimeter coupling devices 1131 and a center coupling device 1133. In the illustrated embodiment, the perimeter coupling devices 1131 and a center coupling device 1133 are the in form of through holes that are configured to receive pins 1170 and a center pin 1172, respectively. Other coupling devices can be implemented as well.

The fourth layer is a bottom chamber layer 1140. The bottom chamber layer can be formed of PDMS like the top chamber layer 1120. The bottom chamber layer 1140 includes a first bottom chamber 1142 that receives the fluid that has passed through the first flexible filter array 1101. The first bottom chamber 1142 can be coupled to the second bottom chamber 1144 by a coupling pathway 1162. The fluid in the second bottom chamber 1144 then passes through second flexible filter array 1102. After the fluid has passed through the third flexible filter array 1103, the fluid enters the third bottom chamber 1146. The third bottom chamber 1146 can be coupled to the fourth bottom chamber 1148 by a coupling pathway 1164. Fluid in the fourth bottom chamber pass through the fourth flexible filter array 1104 before entering the fourth top fluid chamber 1128.

A fifth layer can be a base layer 1150. As illustrated the bottom acrylic layer serves as a base for the filter device. The pins 1170 and center pin 1172 can be coupled or affixed to the base layer 1150. In other embodiments, other bases or materials for the base and top portion can be implemented. Furthermore, while four chambers and flexible filter arrays 100 are illustrated, the filter device can implement a greater or lesser number according to the desired filtration scheme.

While the filter device is shown arranged with a series of chambers, the filter device could instead be constructed using a series of stacked layers of flexible filter arrays separated from one another. For example, the flexible filter array layers can be separated by spacers. Alternatively, a series of stacked chambers could be implemented. When the flexible filter array layers are stacked, it can be advantageous as the amount of pressure is reduced.

FIG. 12 illustrates one example of using the tandem filtration device, to separate different subtypes of the leukocytes. Gap widths of 5.9, 4.3, and 1.9 µm were chosen for the three filter patches in the tandem device. Granulocyte-to-lymphocyte-ratio was measured to be 3.3 on the 5.9 µm gap-width patch, while the lymphocyte-to-granulocyte-ratio was 2.5 on the 1.9 µm gap-width patch. The non-ideal separation is due to the size overlap (~30% lymphocytes are "large" lymphocytes and comparable to small granulocytes) and complication of monocytes (largest leukocytes but identified as mononuclear cells in acridine orange staining).

Figure 13A:
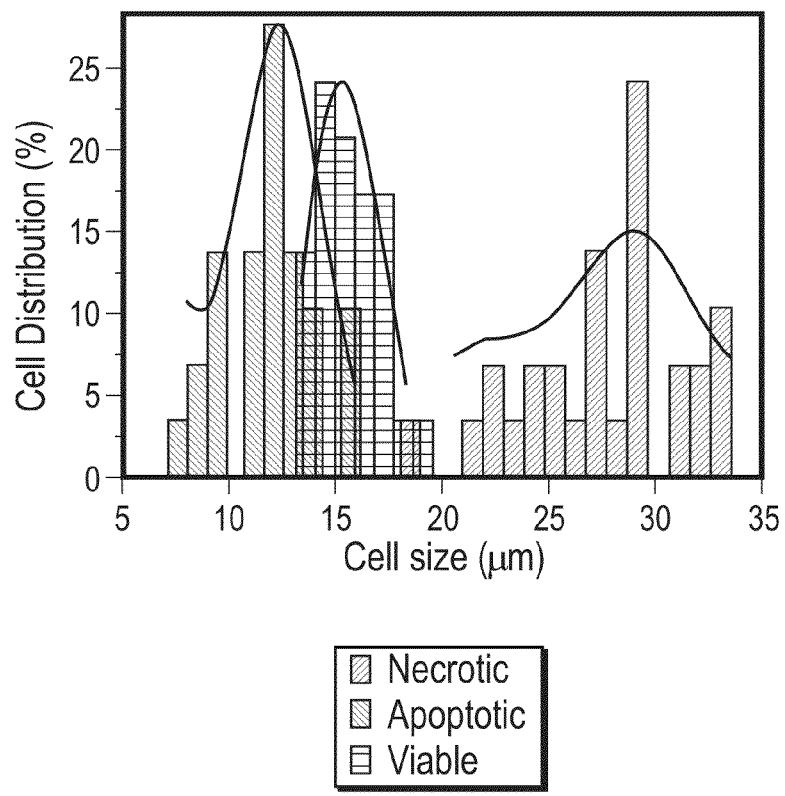
Figure 13B:
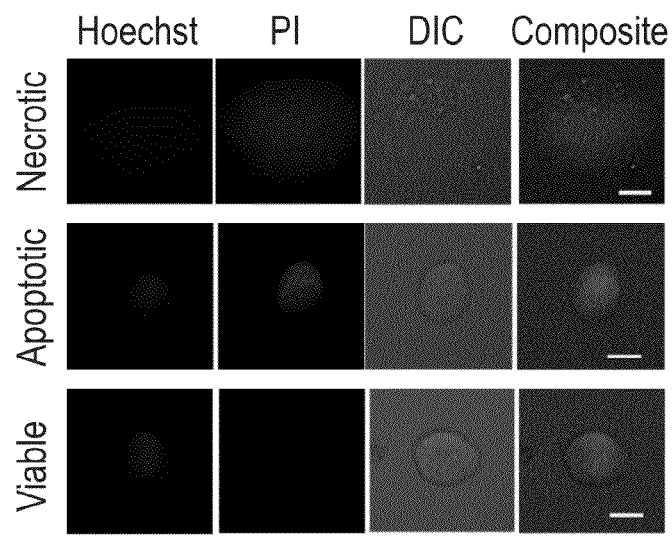

FIG. 13A-F illustrates another example of using the tandem filtration device, to separate viable cells and cells died from different mechanisms. Serum starvation can result cell death in tumor cells. FIG. 13A illustrates a measured cell size distribution. FIG. 13B illustrates fluorescence and differential interference contrast (DIC) microscopic images for cell death detection. FIG. 13C illustrates separation of viable, apoptotic and necrotic cells by a tandem filter array as described herein. Viable, apoptotic and necrotic cells can be detected with fluorescent vital stains. Three distinct populations of cells are found to have different cell size distribution, with necrotic cells the largest, apoptotic cells the smallest and viable cells in between (FIG. 13A and FIG. 13B). FIGS. 13D-F illustrate composite fluorescence images of separate cells on each flexible filter array. Tandem filtration device with gap widths of 1.5 µm (FIG. 13D), 3.5 µm (FIG. 13E), and 5.5 µm (FIG. 13F) were used to fractionate tumor cells after serum starvation. Approximately 90% of the necrotic cells are found on 5.5 µm gap width filter patch and none on 1.5 µm GW patch, while over 50% of the apoptotic cells are found on 1.5 µm gap width filter patch and none on 5.5 µm gap width filter patch (FIG. 13D-F).

Figure 14A:
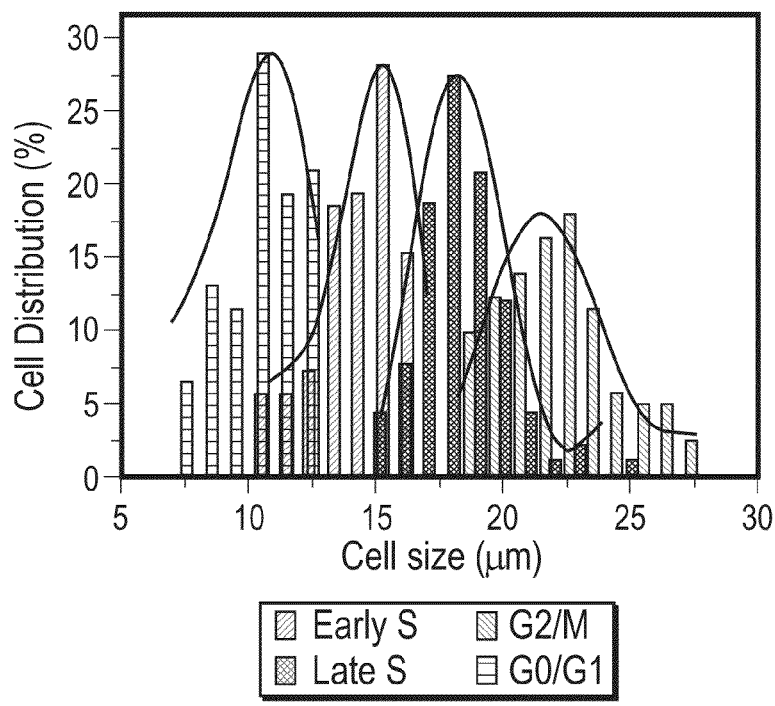
Figure 14B:
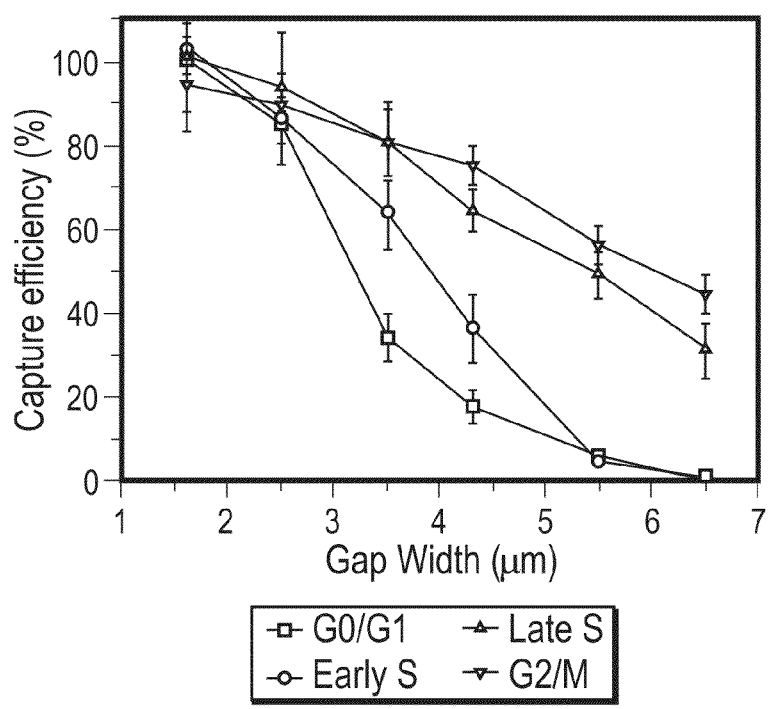

FIG. 14A-F illustrates another example of using the tandem filtration device, to separate cells of the same type but at different cell cycles. FIG. 14A illustrated measured size distribution at different stages of the cell cycle. FIG. 14B illustrates capture efficiency of cells at different stages of the cell cycle by a single flexible filter array of a varying gap widths. FIG. 14C illustrates a separation of early S (red fluorescence labeled) and G2/M (green fluorescence labeled) stage cells by a tandem flexible filter array. FIGS. 14D-F illustrate composite fluorescence microscopic images of polylactic acid, polyglycolide, or any other micromachinable biodegradable material with gap widths of 2.5 µm (FIG. 14D), 4.3 µm (FIG. 14E), and 6.5 µm (FIG. 14F). Mammalian cell's volume changes during the cell cycle, with the smallest of newly born cells in G1 phase and largest before mitosis in the G2 phase. As a heterogeneous population, cells might be in different phases of cell cycle and this may contribute to cell size variation. In fact, size based separation is an effective physical approach for cell synchronization. MDA-MB-231 cells are synchronized at different cell cycle stages: G0/G1 stage by serum starvation, early S stage by double thymidine (dT) block, late S stage by lease after dT block and G2/M stage by thymidine-nocodazale block. Cell size distributions of individual cell population (FIG. 14A) and the capture efficiency of single FMSA device with different gap widths for each cell population (FIG. 14B) were measured. Based on this information, gap widths of the filters inside the tandem device were chosen. 99% of the cells on 6.5 µm gap width FMSA patch are at G2/M stage, while the ratio of cells in Early S to those in G2/M stage is ~10 on the 2.5 μm gap width FMSA patch.

While the above embodiments and examples are provided, it is appreciated that this disclosure is for a flexible filter array according to the teachings as supplied herein. Specifically, other configurations and arrays of flexible filter arrays can be made and remain within the scope of this disclosure.

What is claimed is:

1. A filtering device comprising:
   a housing;
   one or more flexible filter arrays coupled to the housing, each flexible filter array comprising:
      a plurality of members being spaced apart by a predetermined distance wherein one or more of the plurality of members comprise two or more adjacent members that have axes that are substantially parallel to one another, and the two or more adjacent members are separated by a gap space formed therebetween;
      one or more support members to which one or more of the plurality of members are coupled;
      each of the plurality of members is configured to deflect relative to the one or more support members,
      wherein two of the two or more adjacent members are coupled to one another via a connecting portion.

2. The filtering device as recited in claim 1, wherein the plurality of members are substantially rigid.

3. The filtering device as recited in claim 1, wherein one or more of the plurality of members are substantially straight.

4. The filtering device as recited in claim 1, wherein the connecting portion is substantially perpendicular to the two of the two or more adjacent members.

5. The filtering device as recited in claim 4, wherein the connecting portion is substantially straight.

6. The filtering device as recited in claim 1, wherein the plurality of members form a gap space therebetween and the at least one flexible filter array has a porosity between twenty to sixty percent, the porosity being a ratio of an area of the gap space relative to a total exposed surface area of the flexible filter array.

7. The filter device as recited in claim 6, wherein the porosity is between forty and sixty percent.

8. The filter device as recited in claim 6, wherein the porosity is between fifty and sixty percent.

9. The filter device as recited in claim 1, wherein at least one flexible filter array has a through flow direction in a first direction, the deflection of the plurality of members being in the first direction.

10. The filter device as recited in claim 9, wherein at least one flexible filter array is substantially non-deformable in a second direction that is orthogonal to the first direction.

11. The filter device as recited in claim 1, wherein one or more of the plurality of members are substantially straight and are each spaced apart by a distance between 1 and 50 micrometers.

12. The filtering device as recited in claim 1, wherein the two or more adjacent members are spaced apart by a distance between 3 and 9 micrometers.

13. The filtering device as recited in claim 1, wherein the plurality of members are constructed from at least one of parylene-C, polydimethylsiloxane, and polyimide.

14. The filtering device as recited in claim 1, wherein at least one flexible filter array is operable to filter whole blood at flow rate between 0.1 mL/min and 50 mL/min and a pressure less than 1245 Pa.

15. The filtering device as recited in claim 1, wherein at least one flexible filter array is operable to filter whole blood at flow rate between 0.1 mL/min and 50 mL/min and a pressure less than 249 Pa.

16. The filtering device as recited in claim 1, wherein the one or more flexible filter arrays comprise two flexible filter arrays wherein each of the flexible filter arrays is formed such that the predetermined distance between members of a first flexible filter array is different than the predetermined distance between members of a second flexible filter array.

17. The filter device as recited in claim 1, wherein at least one flexible filter array is configured to filter blood such that particles and cells circulating in the blood larger than a predetermined diameter are prevented from passing through the filter.

18. The filtering device as recited in claim 1, wherein the plurality of members are constructed from a micromachinable thin-film material.

19. The filtering device as recited in claim 18, wherein the thin-film material is transparent.

* * * * *